US005962504A

United States Patent [19]
Kozikowski et al.

[11] Patent Number: 5,962,504
[45] Date of Patent: Oct. 5, 1999

[54] SUBSTITUTED 2-PYRROLIDINONE ACTIVATORS OF PKC

[75] Inventors: Alan P. Kozikowski, Princeton, N.J.; Shaomeng Wang, McLeane, Va.; Lixin Qiao, Washington, D.C.

[73] Assignee: Georgetown University, Washington, D.C.

[21] Appl. No.: 09/149,609

[22] Filed: Sep. 8, 1998

Related U.S. Application Data

[60] Provisional application No. 60/058,139, Sep. 8, 1997.

[51] Int. Cl.$^6$ .......................... A61K 31/40; C07D 207/26
[52] U.S. Cl. ........................ 514/424; 548/217; 548/407; 548/546; 548/547
[58] Field of Search ...................................... 514/256, 314, 514/343, 381, 391, 408, 422, 424; 544/335; 546/152, 164, 278.4; 548/252, 314.7, 518, 546, 547, 551

[56] References Cited

U.S. PATENT DOCUMENTS

| | | | |
|---|---|---|---|
| 4,559,157 | 12/1985 | Smith et al. | 252/90 |
| 4,608,392 | 8/1986 | Jacquet et al. | 514/844 |
| 4,820,508 | 4/1989 | Wortzman | 424/59 |
| 4,992,478 | 2/1991 | Geria | 514/782 |
| 5,348,970 | 9/1994 | Schwartz et al. | 514/422 |
| 5,541,343 | 7/1996 | Himmelsbach et al. | 514/424 |
| 5,591,769 | 1/1997 | Himmelsbach et al. | 514/423 |
| 5,672,621 | 9/1997 | Alfatafta et al. | 514/422 |

OTHER PUBLICATIONS

Hashimoto et al., A Steroselective Synthesis of a Novel Model Compound of Carzinophilin, Chemistry Letters, (6), pp. 1001–1002, 1994.

Okumura et al., Isolation and Structural Investigation of the Chromophore in the Fujiwara Reaction as Applied to Chloramphenicol, Chem. Pharm. Bull., 31(8), pp. 2737–2742. 1983.

Sato et al., Synthesis of a Simple Kainic Acid Analogue by Means of Carbamoylmethyl Radical Cyclization, Heterocycles, vol. 40(1), pp. 261–270, 1995.

Brackeen, M.F., et al., "Design and synthesis of conformationally constrained analogues of 4–(3–Butoxy–4–methoxybenzyl) imidazolidin–2–one (Ro 20–1724) as potent inhibitors of cAMP–specific phosphodiesterase", *J. Med. Chem.*, Vo. 38, pp. 4848–4854, (1995).

Okumura, K., et al., "Isolation and structural investigation of the chromophore in the Fujiwara reaction as applied to chloramphenicol", *Chem. Pharm. Bull.*, vol. 31, No. 8, pp. 2737–2742, (1983).

Posner, G.H., et al., "Nitroolefins in one–flask, tandem, A+B+C coupling reactions producing heterocycles", *Tetrahedron (Incl. Tetrahedron Reports)*, vol. 46, No. 21, pp. 7509–7530, (1990).

Silverman, R.B., et al., "Selective inhibition of gamma–aminobutyric acid aminotransferase by (3R,4R), (3S,4S)–and (3R, 4S), (3S,4R)–4amino–5–fluoro–3phenylpentanoic acids", *Journal of Medicinal Chemistry*, vol. 23, No. 3, pp. 931–936, (1990).

Ahmad, S., et al., "Antisense Expression of Protein Kinase Cα Inhibits the Growth and Tumorigenicity of Human Glioblastoma Cells", *Neurosergery*, vol. 35, No. 5, pp. 904–909, (Nov. 1994).

Ashendel, C.L., et al., "Protein Kinase Activity Associated with a Phorbol Ester Receptor Purified from Mouse Brain", *Cancer Research*, vol. 43, pp. 4333–4337, (Sep. 1983).

Blobe, G.C., et al., "Regulation of Protein Kinase C and Role in Cancer Biology", *Cancer and Metastasis Reviews*, vol. 13, Nos. 3–4, pp. 411–431, (1994).

Dean, N.M., et al., "Inhibition of Protein Kinase C–α Expression in Human A549 Cells by Antisense Oligonucleotides Inhibits Induction of Intercellular Adhesion Molecule 1 (ICAM–1) mRNA by Phorbol Esters", *The Journal of Biochemical Chemistry*, vol. 269, No. 23, pp. 16416–16424, (Jun. 10, 1994).

Gesher, A., "Towards Selective Pharmacological Modulation of Protein Kinase C–Opportunites for the Development of Novel Antineoplastic Agents", *British Journal of Cancer*, vol. 66, No. 1, pp. 10–19, (Jul. 1992).

Glazer, R.I., "Protein Kinase C in Multidrug Resistance, Neoplastic Transformation, and Differentiation", *Protein Kinase C*, New York Oxford Oxford University Press, pp. 171–198, (1994).

House, C., et al., "Protein Kinase C Contains a Pseudosubstrate Protope in Its Regulatory Domain", *Science*, vol. 238, No. 4834, pp. 1726–1728, (Dec. 18, 1987).

Hug, H., et al., "Protein Kinase C Isoenzymes: Divergence in Signal Transduction?", *Biochemical Journal*, vol. 291, pp. 329–343, (Apr. 15, 1993).

Kikkawa, U., et al., "Calcium–activated, Phospholipid–dependent Protein Kinase from Rat Brain", *The Journal of Biological Chemistry*, vol. 257, No. 22, pp. 13341–13348, (Nov. 25, 1982).

(List continued on next page.)

Primary Examiner—Robert W. Ramsuer
Assistant Examiner—John L. Wok
Attorney, Agent, or Firm—Schwegman, Lundberg, Woessner, and Kluth, P.A.

[57] ABSTRACT

Compounds of formula I:

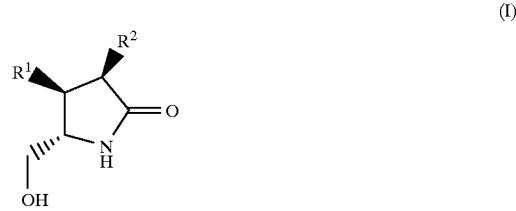

wherein $R_1$ and $R_2$ have any of the values defined in the specification, and their pharmaceutically acceptable salts, are PKC activators and are useful for treating diseases, such as, for example, cancer. Also disclosed are pharmaceutical compositions comprising compounds of formula I, processes for preparing compounds of formula I, and intermediates useful for preparing compounds of formula I.

16 Claims, 6 Drawing Sheets

OTHER PUBLICATIONS

Kikkawa, U., et al., "The Protein Kinase C Family: Heterogeneity and Its Implications", *Annual Reveiw of Bichemistry*, vol. 58, pp. 31–44, (1989).

Kozikowski, A.P., et al., "Modeling, chemistry, and biology of the benzolactam analogues of indolactam VOILV). 2. Identification of the binding site of the benzolactams in the CRD activator–binding domain of PKCπ and Discovery of an ILV analogue of improved isozyme selectivity", *J. MEd. Chem.*, vol. 40, pp. 1316–1326, (1997).

Nishizuka, Y., "Studies and Prospectives of the Protein Kinase C Family for Cellular Regulation", *Cancer*, vol. 63, pp. 1892–1903, (May 15, 1989).

Qiao, L., et al., "Structure–Based Design of a New Class of Protein Kinase C Modulators", *Journal of the American Chemical Society*, vol. 120, No. 26, pp. 6629–6630, (Jul. 8, 1998).

Brackeen, M.F., et al., "Design and synthesis of conformationally constrained analogues of 4–(3–Butoxy–4–methoxybenzyl) imidazolidin–2–one (Ro 20–1724) as potent inhibitors of cAMP–specific phosphodiesterase", *J.Med. Chem.*, Vo. 38, pp. 4848–4854, (1995).

Okumura, K., et al., "Isolation and structural investigation of the chromophore in the Fujiwara reaction as applied to chloramphenicol", *Chem. Pharm. Bull.*, vol. 31, No. 8, pp. 2737–2742, (1983).

Posner, G.H., et al., "Nitroolefins in one–flask, tandem, A+B+C coupling reactions producing heterocycles", *Tetrahedron (Incl. Tetrahedron Reports)*, vol. 46, No. 21, pp. 7509–7530, (1990).

Silverman, R.B., et al., "Selective inhibition of gamma–aminobutyric acid aminotransferase by (3R,4R), ((3S,4S)–and (3R, 4S), (3S, 4R)–4amino–5–fluoro–3phenylpentanoic acids", *Journal of Medicinal Chemistry*, vol. 23, No. 3, pp. 931–936, (1990).

4a R=H
4b R=nonyl

15a R"=R'"=Me R=nonanoyloxy
15b R"=R'"=H; R=nonanoyloxy
15c R"=R'"=H; R=hexanoyloxy
15d R" and R'"=cyclopropyl;
    R=nonanoyloxy 14a R"=R'"=Me; R=nonanoyloxy
14b R"=R'"=H; R=nonanoyloxy
14c R"=R'"=H; R=hexanoyloxy
14d R" and R'"=cyclopropyl;
    R=nonanoyloxy

SUBSTITUTED 2-PYRROLIDINONE ACTIVATORS OF PKC

PRIORITY OF INVENTION

This application claims priority under 35 U.S.C. §119(e) from U.S. Provisional Application Number 60/058,139, filed on Sep. 08, 1997.

GOVERNMENT SUPPORT

This invention was made with U.S. Government support under DAMD17-93-V-3018 awarded by the Department of Defense and CA61015 awarded by the National Institutes of Health. The Government has certain rights in the invention.

BACKGROUND OF THE INVENTION

Protein kinases serve a regulatory function which is crucial for all aspects of cellular development, differentiation and transformation. One of the largest gene families of non-receptor serine-threonine protein kinases is protein kinase C (PKC). Since the discovery of PKC more than a decade ago by Nishizuka and coworkers (Kikkawa et al., *J. Biol. Chem.*, 257, 13341 (1982)), and its identification as a major receptor for phorbol esters (Ashendel et al., *Cancer Res.*, 43, 4333 (1983)), a multitude of physiological signaling mechanisms have been ascribed to this enzyme. The intense interest in PKC stems from its unique ability to be activated in vitro by diacylglycerol (and its phorbol ester mimetics), an effector whose formation is coupled to phospholipid turnover by the action of growth and differentiation factors.

The PKC gene family consists presently of 11 genes which are divided into four subgroups: 1) classical PKCα, $\beta_1$, $\beta_2$ ($\beta_1$ and $\beta_2$ are alternately spliced forms of the same gene) and γ, 2) novel PKCδ, ε, η, and θ, 3) atypical PKCζ, λ, η and ι and 4) PKCμ. PKCμ resembles the novel PKC isoforms but differs by having a putative transmembrane domain (reviewed in Blobe et al., *Cancer Metast. Rev.*, 13, 411 (1994)); Hug et al., *Biochem J.*, 291, 329 (1993); Kikkawa et al., *Ann. Rev. Biochem*, 58, 31 (1989)). The α, $\beta_1$, $\beta_2$ and γ isoforms are $Ca^{2+}$, phospholipid- and diacylglycerol-dependent and represent the classical isoforms of PKC, whereas the other isoforms are activated by phospholipid and diacylglycerol but are not dependent on $Ca^{2+}$. All isoforms encompass 5 variable (V1–V5) regions, and the α, β and γ isoforms contain four (C1–C4) structural domains which are highly conserved. All isoforms except PKCα, β, and γ lack the C2 domain, and the λ, η and ι isoforms also lack one of two cysteine-rich zinc finger domains in C1 to which diacylglycerol binds. The C1 domain also contains the pseudosubstrate sequence which is highly conserved among all isoforms, and which serves an autoregulatory function by blocking the substrate-binding site to produce an inactive conformation of the enzyme (House et al. *Science*, 238, 1726 (1987)).

Because of these structural features, diverse PKC isoforms are thought to have highly specialized roles in signal transduction in response to physiological stimuli (Nishizuka, *Cancer*, 10, 1892 (1989)), as well as in neoplastic transformation and differentiation (Glazer, *Protein Kinase C*, J. F. Kuo, ed., Oxford U. Press (1994) at pages 171–198.

From a pharmacological perspective, PKC has served as a focal point for the design of anticancer drugs (Gescher, *Brit. J. Cancer*, 66, 10 (1992)). Antisense expression of either the PKCα cDNA (Ahmad et al., *Neurosurgery*, 35, 904 (1994)) or a phosphorothioate oligodeoxynucleotide (S-oligo) for PKCα has shown the efficacy of targeting PKC to inhibit the proliferation of A549 lung carcinoma cells (Dean et al., *J. Biol. Chem.*, 269, 16416 (1994)) and U-87 glioblastoma cells. However, it is not clear which isoforms are most crucial for tumor proliferation and what role different PKC isoforms play in such critical cellular processes as cell proliferation and apoptosis.

Investigations with 12-O-tetradecanoylphorbol-13-acetate (TPA) have provided considerable information on tumor promotion. In the two stage model of skin carcinogenesis, it is believed that initiators bind to DNA and that tumor promoters such as TPA bind non-covalently to membrane-associated high affinity receptors, most likely protein kinase C. Thus, TPA, as well as the known teleocidins, lyngbyatoxins, and aplysiatoxin serve as diacylglycerol mimics, binding to the diacylglycerol site of protein kinase C, thus activating the kinase.

In view of the central role that PKC plays in tumor promotion and signal transduction, PKC is an exciting target for cancer therapy. Oncogenes like src, ras, and sis, elevate phosphatidylinositol turnover; transcription of cellular protooncogenes, including myc, and fos, is mediated by PKC; PKC regulates the activity of the transcriptional activator protein c-jun, and stimulates the mutidrug resistance system. There is increasing evidence that the individual PKC isozymes play different, sometimes opposing, roles in biological processes, providing two directions for pharmacological exploitation. One is the design of specific (peferrably, isozyme specific) inhibitors of PKC. This approach is complicated by the fact that the catalytic domain is not the domain primarily responsible for the isotype specificity of PKC. The other approach is to develope isozyme-selective, regulatory site-directed PKC activators. These may provide a way to override the effect of other signal transduction pathways with opposite biological effects. Alternatively, by inducing down-regulation of PKC after acute activation, PKC activators may cause long term antagonism. Dpp (12-deoxyphorbol 13-phenylacetate) and bryostatin are examples of isozyme-selective activators of PKC. Bryostatin is currently in clinical trials as an anti-cancer agent. The bryostatins are known to bind to the regulatory domain of PKC and to activate the enzyme. In mouse skin, they act as strong inhibitors of first stage tumor promotion, and modest inhibitors of complete tumor promotion.

There is a continuing need for novel compounds which can activate PKC. Such compounds may be useful, for example, to effect the selective killing of cancer cells.

SUMMARY OF THE INVENTION

The present invention provides certain substituted 2-pyrrolidinones that are PKC activators. Accordingly, the invention provides a compound of the invention which is a compound of formula I:

wherein $R^1$ and $R^2$ are each independently $(C_1–C_{15})$alkyl, $(C_2–C_{15})$alkenyl, $(C_2–C_{15})$alkynyl, $(C_3–C_8)$cycloalkyl, $(C_3-C_8)$cycloalkyl$(C_1-C_{10})$alkyl, $(C_3-C_8)$cycloalkyl $(C_1-C_{15})$alkenyl, $(C_3-C_8)$cycloalkyl$(C_1-C_{15})$alkynyl, $(C_1-C_{15})$alkoxy, $(C_1-C_{15})$alkanoyl, $(C_1-C_{15})$ alkanoyloxy, aryl, heteroaryl, aryl$(C_1-C_6)$alkyl, heteroaryl$(C_1-C_6)$alkyl, aryl$(C_2-C_{15})$alkenyl, heteroaryl$(C_2-C_{15})$alkenyl, aryl$(C_2-C_{15})$alkynyl, heteroaryl$(C_2-C_{15})$alkynyl, aryl$(C_1-C_{15})$alkoxy, heteroaryl$(C_1-C_{15})$alkoxy, aryl$(C_1-C_{15})$alkanoyl, heteroaryl$(C_1-C_{15})$alkanoyl, aryl$(C_1-C_{15})$alkanoyloxy, or heteroaryl$(C_1-C_{15})$alkanoyloxy;

wherein any $R^1$ or $R^2$ is optionally substituted with one or more (e.g. 1, 2, 3, or 4) substituents independently selected from the group consisting of halo, nitro, cyano, hydroxy, trifluoromethyl, trifluoromethoxy, $(C_1-C_{15})$ alkyl, $(C_2-C_{15})$alkenyl, $(C_2-C_{15})$alkynyl, $(C_3-C_8)$ cycloalkyl, $(C_3-C_8)$cycloalkyl$(C_1-C_{15})$alkyl, $(C_3-C_8)$ cycloalkyl-$(C_2-C_{15})$alkenyl, $(C_3-C_8)$cycloalkyl $(C_2-C_{15})$alkynyl, $(C_1-C_{15})$alkoxy, $(C_1-C_{15})$alkanoyl, $(C_1-C_{15})$alkanoyloxy, $C(=O)OR_a$, $C(=O)NR_bR_c$, $OC(=O)OR_a$, $OC(=O)NR_bR_c$, and $NR_eR_f$; and wherein any aryl or heteroaryl of $R^1$ or $R^2$ is optionally substituted on a non-aromatic carbon by a divalent $(C_2-C_7)$alkylene chain to form a $(C_3-C_8)$ spirocycloalkyl;

each $R_a$ is independently hydrogen or $(C_1-C_6)$alkyl;

each $R_b$ and $R_c$ is independently, hydrogen or $(C_1-C_{10})$ alkyl; or $R_b$, and $R_c$ together with the nitrogen to which they are attached are a 5–6 membered heterocyclic ring; and each $R_c$ and $R_f$ is independently hydrogen, $(C_1-C_{10})$alkyl, $(C_1-C_{10})$alkanoyl, phenyl, benzyl, or phenethyl; or $R_c$ and $R_f$ together with the nitrogen to which they are attached are a 5–6 membered heterocyclic ring;

or a pharmaceutically acceptable salt thereof.

The invention also provides pharmaceutical compositions comprising a compound of the invention, processes for preparing compounds of the invention and novel intermediates useful for the synthesis of compounds of the invention.

The invention also provides a therapeutic method comprising treating a condition characterized by the pathological proliferation of mammalian cells (e.g. cancer) by administering to a mammal afflicted with such a condition, an effective amount of a compound of claim 1.

The invention also provides a method comprising modulating PKC in a mammal by administering to said mammal an effective dose of a compound of claim 1; or a pharmaceutically acceptable salt thereof.

The invention also provides a compound of formula I for use in medical therapy (preferably for use in treating cancer), as well as the use of a compound of formula I for the manufacture of a medicament for the treatment of cancer (e.g. tumors).

It is reasonable to conclude that isoform selective, non-tumor promoting activators of PKC that cause downregulation may find use in cancer treatment through the initiation of cancer cell death through apoptosis. Selective cancer cell killing may be achieved either through the targeting of those isoforms found to be overexpressed in the cancer cells, or through the synergistic interaction of a cytotoxic drug like 1-β-D-arabinofuranosylcytosine with an appropriate PKC-based signaling interceptor.

Because of their ability to activate PKC, compounds of the invention may also be useful as pharmacological tools for the in vitro or in vivo study of the physiological function and effects of the PKC gene family.

Brief Description of the FIGS.

FIG. 1 illustrates the preparation of representative compounds of the invention.
FIG. 2 illustrates the preparation of representative compounds of the invention.
FIG. 3 illustrates the preparation of representative compounds of the invention.
FIG. 4 illustrates the preparation of compounds of formula I and shows intermediates useful for preparing compounds of formula I.
FIG. 5 illustrates the preparation of compounds of formula I and shows intermediates useful for preparing compounds of formula I.
FIG. 6 illustrates intermediates useful for preparing compounds of formula I

DETAILED DESCRIPTION OF THE INVENTION

Figure 1:
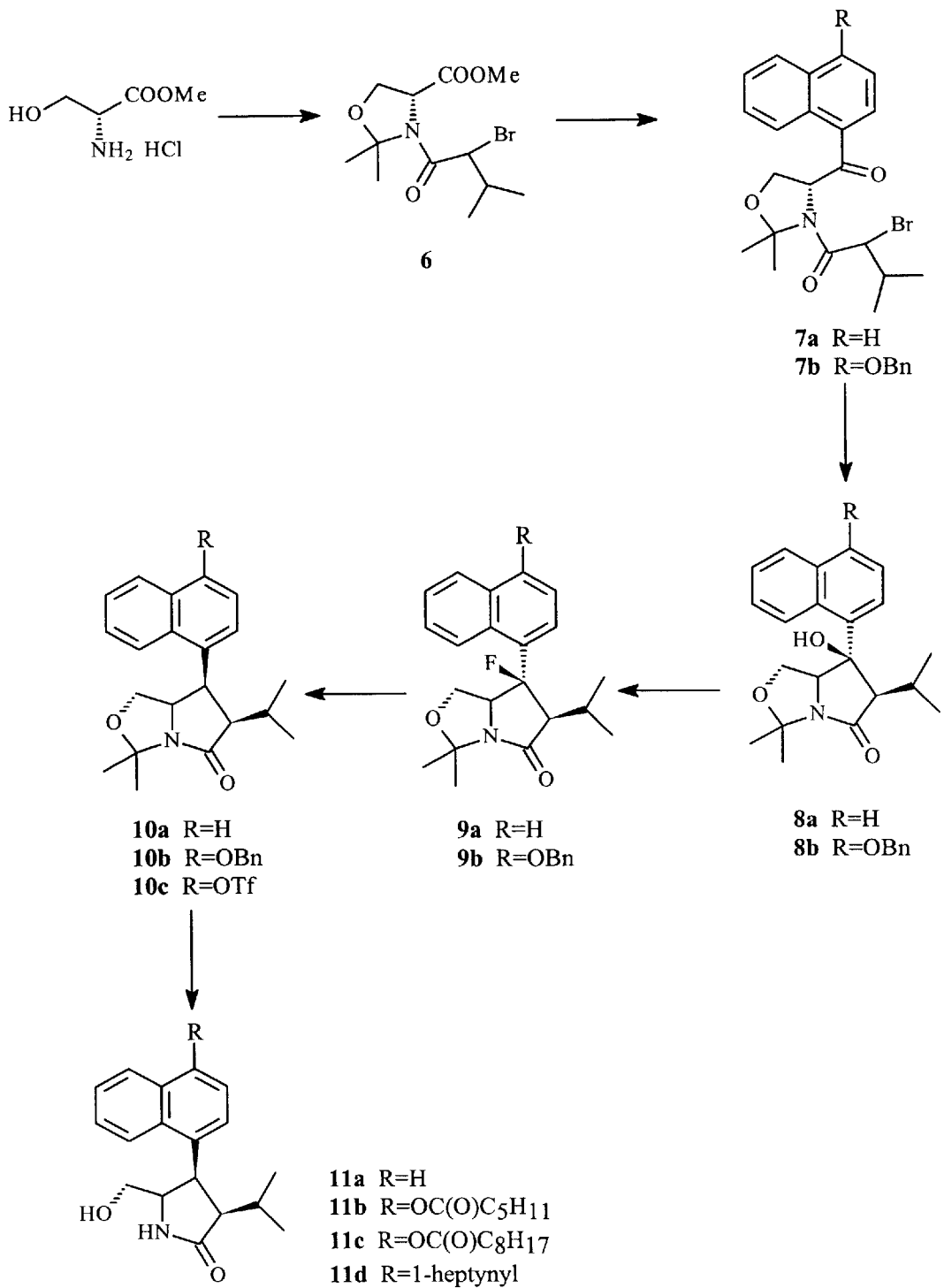

The following definitions are used, unless otherwise described. Halo is fluoro, chloro, bromo, or iodo. Alkyl, alkoxy, etc. denote both straight and branched groups; but reference to an individual radical such as "propyl" embraces only the straight chain radical, a branched chain isomer such as "isopropyl" being specifically referred to. Aryl denotes a phenyl radical or an ortho-fused bicyclic carbocyclic radical having about nine to ten ring atoms in which at least one ring is aromatic. Heteroaryl encompasses a radical attached via a ring carbon of a monocyclic aromatic ring containing five or six ring atoms consisting of carbon and one to four heteroatoms each selected from the group consisting of non-peroxide oxygen, sulfur, and $N(R_x)$ wherein $R_x$ is absent or is hydrogen, oxo, $(C_1-C_4)$alkyl, phenyl or benzyl, as well as a radical of an ortho-fused bicyclic heterocycle of about eight to ten ring atoms derived therefrom, particularly a benz-derivative or one derived by fusing a propylene, trimethylene, or tetramethylene diradical thereto.

It will be appreciated by those skilled in the art that compounds of the invention having one or more chiral center(s) may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis, from optically-active starting materials, by chiral synthesis, or by chromatographic separation using a chiral stationary phase) and how to determine the ability of a compound to activate PKC using the tests described herein, or using other tests which are well known in the art. The preferred absolute configuration for compounds of the invention is that shown in formula I above.

Specific and preferred values listed below for radicals, substituents, and ranges, are for illustration only; they do not exclude other defined values or other values within defined ranges for the radicals and substituents.

Specifically, $(C_1-C_{15})$alkyl can be methyl, ethyl, propyl, isopropyl, butyl, iso-butyl, sec-butyl, pentyl, 3-pentyl, hexyl, heptyl, octyl, nonyl, decyl, undecyl, dodecyl, tridecyl, tetradecyl or pentadecyl; $(C_1-C_6)$alkyl can be methyl, ethyl, propyl, isopropyl, butyl, iso-butyl, sec-butyl, pentyl, 3-pentyl, or hexyl; $(C_2-C_{15})$alkenyl can be vinyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, 1-heptenyl, 2-heptenyl, 3-heptenyl, 4-heptenyl, 5-heptenyl, 6-heptenyl, 1-octenyl, 2-octenyl, 3-octenyl, 4-octenyl, 5-octenyl, 6-octenyl, 7-octenyl, 1-nonenyl, 2-nonenyl, 3-nonenyl, 4-nonenyl, 5-nonenyl, 6-nonenyl, 7-nonenyl, 8-nonenyl, 1-decenyl, 2-decenyl, 3-decenyl, 4-decenyl, 5-decenyl, 6-decenyl, 7-decenyl, 8-decenyl, 9-decenyl; 1-undecenyl, 2-undecenyl, 3-undecenyl, 4-undecenyl, 5-undecenyl, 6-undecenyl, 7-undecenyl, 8-undecenyl, 9-undecenyl, 10-undecenyl, 1-dodecenyl, 2-dodecenyl, 3-dodecenyl, 4-dodecenyl, 5-dodecenyl, 6-dodecenyl, 7-dodecenyl, 8-dodecenyl, 9-dodecenyl, 10-dodecenyl, 11-dodecenyl, 1-tridecenyl, 2-tridecenyl, 3-tridecenyl, 4-tridecenyl, 5-tridecenyl, 6-tridecenyl, 7-tridecenyl, 8-tridecenyl, 9-tridecenyl, 10-tridecenyl, 11-tridecenyl, 12-tridecenyl, 1-tetradecenyl, 2-tetradecenyl, 3-tetradecenyl, 4-tetradecenyl, 5-tetradecenyl, 6-tetradecenyl, 7-tetradecenyl, 8-tetradecenyl, 9-tetradecenyl, 10-tetradecenyl, 11-tetradecenyl, 12-tetradecenyl, 13-tetradecenyl, 1-pentadecenyl, 2-pentadecenyl, 3-pentadecenyl, 4-pentadecenyl, 5-pentadecenyl, 6-pentadecenyl, 7-pentadecenyl, 8-pentadecenyl, 9-pentadecenyl, 10-pentadecenyl, 11-pentadecenyl, 12-pentadecenyl, 13-pentadecenyl, 14-pentadecenyl; ($C_2$–$C_6$) alkenyl can be vinyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl; ($C_2$–$C_{15}$)alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, 1-heptynyl, 2-heptynyl, 3-heptynyl, 4-heptynyl, 5-heptynyl, 6-heptynyl, 1-octynyl, 2-octynyl, 3-octynyl, 4-octynyl, 5-octynyl, 6-octynyl, 7-octynyl, 1-nonynyl, 2-nonynyl, 3-nonynyl, 4-nonynyl, 5-nonynyl, 6-nonynyl, 7-nonynyl, 8-nonynyl, 1-decynyl, 2-decynyl, 3-decynyl, 4-decynyl, 5-decynyl, 6-decynyl, 7-decynyl, 8-decynyl, 9-decynyl, 1-undecynyl, 2-undecynyl, 3-undecynyl, 4-undecynyl, 5-undecynyl, 6-undecynyl, 7-undecynyl, 8-undecynyl, 9-undecynyl, 10-undecynyl, 1-dodecynyl, 2-dodecynyl,3-dodecynyl, 4-dodecynyl, 5-dodecynyl, 6-dodecynyl, 7-dodecynyl, 8-dodecynyl, 9-dodecynyl, 10-dodecynyl, 11-dodecynyl, 1-trideynyl, 2-tridecynyl, 3-tridecynyl, 4-tridecynyl, 5-tridecynyl, 6-tridecynyl, 7-tridecynyl, 8-tridecynyl, 9-tridecynyl, 10-tridecynyl, 11-tridecynyl, 12-tridecynyl, 1-tetradecynyl, 2-tetradecynyl, 3-tetradecynyl, 4-tetradecynyl, 5-tetradecynyl, 6-tetradecynyl, 7-tetradecynyl, 8-tetradecynyl, 9-tetradecynyl, 10-tetradecynyl, 11-tetradecynyl, 12-tetradecynyl, 13-tetradecynyl, 1-pentadecynyl, 2-pentadecynyl, 3-pentadecynyl, 4-pentadecynyl, 5-pentadecynyl, 6-pentadecynyl, 7-pentadecynyl, 8-pentadecynyl, 9-pentadecynyl, 10-pentadecynyl, 11-pentadecynyl, 12-pentadecynyl, 13-pentadecynyl, 14-pentadecynyl; ($C_1$–$C_{10}$)alkoxy can be methoxy, ethoxy, propoxy, isopropoxy, butoxy, iso-butoxy, sec-butoxy, pentoxy, 3-pentoxy, hexoxy, heptyloxy, octyloxy, nonyloxy, decyloxy, undecyloxy, dodecyloxy, tridecyloxy, tetradecyloxy, or pentadecyloxy; ($C_1$–$C_{15}$)alkanoyl can be acetyl, propanoyl, butanoyl, pentanoyl, hexanoyl, heptanoyl, octanoyl, nonanoyl, decanoyl, undecanoyl, dodecanoyl, tridecanoyl, tetradecanoyl, or pentadecanoyl; ($C_1$–$C_{15}$) alkanoyloxy can be formyloxy, acetoxy, propanoyloxy, butanoyloxy, pentanoyloxy, hexanoyloxy, hepyanoyloxy, octanoyloxy, nonanoyloxy, decanoyloxy, undecanoyloxy, dodecanoyloxy, tridecanoyloxy, tetradecanoylxoy, or pentadecanoyloxy; and ($C_3$–$C_8$)cycloalkyl can be cyclopropyl, cyclobutyl, cyclopentyl, cyclohexyl, cycloheptyl, or cyclooctyl, Aryl can be phenyl, indenyl, 5,6,7,8-tetrahydronaphthyl, or naphthyl and heteroaryl can be furyl, imidazolyl, tetrazolyl, pyridyl, (or its N-oxide), thienyl, pyrimidinyl (or its N-oxide), indolyl, or quinolyl (or its N-oxide).

A specific value for $R^1$ is ($C_1$–$C_{15}$)alkyl, ($C_2$–$C_{15}$)alkenyl, ($C_2$–$C_{15}$)alkynyl, ($C_3$–$C_8$)cycloalkyl, ($C_3$–$C_8$)cycloalkyl($C_1$–$C_{10}$)alkyl, ($C_3$–$C_8$)cycloalkyl($C_1$–$C_{15}$)alkenyl, ($C_3$–$C_8$)cycloalkyl($C_1$–$C_{15}$)alkynyl, ($C_1$–$C_{15}$)alkoxy, ($C_1$–$C_{15}$)alkanoyl, or ($C_1$–$C_{15}$)alkanoyloxy; wherein $R^1$ is optionally substituted with one or more (e.g. 1, 2, 3, or 4)substituents independently selected from the group consisting of halo, nitro, cyano, hydroxy, trifluoromethyl, trifluoromethoxy, ($C_1$–$C_{15}$)alkyl, ($C_2$–$C_{15}$)alkenyl, ($C_2$–$C_{15}$)alkynyl, ($C_3$–$C_8$)cycloalkyl, ($C_3$–$C_8$)cycloalkyl ($C_1$–$C_{15}$)alkyl, ($C_3$–$C_8$)cycloalkyl-($C_2$–$C_{15}$)alkenyl, ($C_3$–$C_8$)cycloalkyl($C_2$–$C_{15}$)alkynyl, ($C_1$–$C_{15}$)alkoxy, ($C_1$–$C_{15}$)alkanoyl, ($C_1$–$C_{15}$)alkanoyloxy, C(=O)OR$_a$, C(=O)NR$_b$R$_c$, OC(=O)OR$_a$, OC(=O)NR$_b$R$_c$, and NR$_e$R$_f$.

Another specific value for $R^1$ is ($C_1$–$C_{15}$)alkyl, ($C_2$–$C_{15}$)alkenyl, ($C_2$–$C_{15}$)alkynyl, ($C_3$–$C_8$)cycloalkyl, ($C_3$–$C_8$)cycloalkyl($C_1$–$C_{10}$)alkyl, ($C_3$–$C_8$)cycloalkyl($C_1$–$C_{15}$)alkenyl, ($C_3$–$C_8$)cycloalkyl($C_1$–$C_{15}$)alkynyl, ($C_1$–$C_{15}$)alkoxy, ($C_1$–$C_{15}$)alkanoyl, or ($C_1$–$C_{15}$)alkanoyloxy; wherein $R^1$ is optionally substituted with one or more (e.g. 1, 2, 3, or 4) substituents independently selected from the group consisting of halo, nitro, cyano, hydroxy, trifluoromethyl, trifluoromethoxy, C(=O)OR$_a$, C(=O)NR$_b$R$_c$, OC(=O)OR$_a$, OC(=O)NR$_b$R$_c$, and NR$_e$R$_f$.

Another specific value for $R^1$ is aryl optionally substituted with 1, 2, or 3 substituents independently selected from the group consisting of halo, nitro, cyano, hydroxy, trifluoromethyl, trifluoromethoxy, ($C_1$–$C_6$)alkyl, ($C_2$–$C_{10}$)alkenyl, ($C_2$–$C_{10}$)alkynyl, ($C_3$–$C_8$)cycloalkyl, ($C_3$–$C_8$)cycloalkyl($C_1$–$C_6$)alkyl, ($C_1$–$C_{10}$)alkoxy, ($C_1$–$C_{10}$)alkanoyl, ($C_2$–$C_{10}$)alkanoyloxy, C(=O)OR$_a$, C(=O)NR$_b$R$_c$, or NR$_e$R$_f$;

Another specific value for $R^1$ is phenyl or naphthyl, optionally substituted with 1, 2, or 3 substituents independently selected from the group consisting of halo, nitro, cyano, hydroxy, trifluoromethyl, trifluoromethoxy, ($C_1$–$C_6$) alkyl, ($C_2$–$C_{10}$)alkenyl, ($C_2$–$C_{10}$)alkynyl, ($C_3$–$C_8$)cycloalkyl, ($C_3$–$C_8$)cycloalkyl($C_1$–$C_6$)alkyl, ($C_1$–$C_{10}$) alkoxy, ($C_1$–$C_{10}$)alkanoyl, ($C_2$–$C_{10}$)alkanoyloxy, C(=O)OR$_a$, C(=O)NR$_b$R$_c$, or NR$_e$R$_f$.

Another specific value for $R^1$ is phenyl or naphthyl, optionally substituted with a substituent selected from the group consisting of halo, nitro, cyano, hydroxy, trifluoromethyl, trifluoromethoxy, ($C_1$–$C_6$)alkyl, ($C_2$–$C_{10}$)alkenyl, ($C_2$–$C_{10}$)alkynyl, ($C_3$–$C_8$)cycloalkyl, ($C_3$–$C_8$)cycloalkyl($C_1$–$C_6$)alkyl, ($C_1$–$C_{10}$alkoxy, ($C_1$–$C_{10}$)alkanoyl, ($C_2$–$C_{10}$)alkanoyloxy, C(=O)OR$_a$, C(=O)NR$_b$R$_c$, or NR$_e$R$_f$.

Another specific value for $R^1$ is aryl, heteroaryl, aryl ($C_1$–$C_6$)alkyl, heteroaryl($C_1$–$C_6$)alkyl, aryl($C_2$–$C_6$)alkenyl, heteroaryl($C_2$–$C_6$)alkenyl, aryl($C_2$–$C_6$)alkynyl, or heteroaryl($C_2$–$C_6$)alkynyl; wherein any aryl or heteroaryl of $R^1$ is optionally substituted with one or more (e.g. 1, 2, 3, or 4) substituents independently selected from the group consisting of halo, nitro, cyano, hydroxy, trifluoromethyl, trifluoromethoxy, ($C_1$–$C_{15}$)alkyl, ($C_2$–$C_{15}$)alkenyl, ($C_2$–$C_{15}$)alkynyl, ($C_3$–$C_8$)cycloalkyl, ($C_3$–$C_8$)cycloalkyl ($C_1$–$C_{15}$)alkyl, ($C_3$–$C_8$)cycloalkyl—($C_2$–$C_{15}$)alkenyl, ($C_3$–$C_8$)cycloalkyl($C_2$–$C_{15}$)alkynyl, ($C_1$–$C_{15}$)alkoxy, $(C_1-C_{15})$alkanoyl, $(C_1-C_{15})$alkanoyloxy, $C(=O)OR_a$, $C(=O)NR_bR_c$, $OC(=O)OR_a$, $OC(=O)NR_bR_c$, and $NR_eR_f$.

Another specific value for $R^1$ is aryl, heteroaryl, aryl$(C_1-C_6)$alkyl, heteroaryl$(C_1-C_6)$alkyl, aryl$(C_2-C_6)$alkenyl, heteroaryl$(C_2-C_6)$alkenyl, aryl$(C_2-C_6)$alkynyl, or heteroaryl$(C_2-C_6)$alkynyl; wherein any aryl or heteroaryl of $R^1$ is optionally substituted with halo, nitro, cyano, hydroxy, trifluoromethyl, trifluoromethoxy, $(C_1-C_{15})$alkyl, $(C_2-C_{15})$alkenyl, $(C_2-C_{15})$alkynyl, $(C_3-C_8)$cycloalkyl, $(C_3-C_8)$cycloalkyl$(C_1-C_{15})$alkyl, $(C_3-C_8)$cycloalkyl—$(C_2-C_{15})$alkenyl, $(C_3-C_8)$cycloalkyl$(C_2-C_{15})$alkynyl, $(C_1-C_{15})$alkoxy, $(C_1-C_{15})$alkanoyl, $(C_1-C_{15})$alkanoyloxy, $C(=O)OR_a$, $C(=O)NR_bR_c$, or $NR_eR_f$.

Another specific value for $R^1$ is aryl or heteroaryl wherein said aryl or heteroaryl is optionally substituted with one or more (e.g. 1, 2, 3, or 4) substituents independently selected from the group consisting of halo, nitro, cyano, hydroxy, trifluoromethyl, trifluoromethoxy, $(C_1-C_{15})$alkyl, $C_2-C_{15}$ alkenyl, $(C_2-C_{15})$alkynyl, $(C_3-C_8)$cycloalkyl, $(C_3-C_8)$cycloalkyl$(C_1-C_{15})$alkyl, $(C_3-C_8)$cycloalkyl-$(C_2-C_{15})$alkenyl, $(C_3-C_8)$cycloalkyl$(C_2-C_{15})$alkynyl, $(C_1-C_{15})$alkoxy, $(C_1-C_{15})$ alkanoyl, $(C_1-C_{15})$alkanoyloxy, $C(=O)OR_a$, $C(=O)NR_bR_c$, $OC(=O)OR_a$, $OC(=O)NR_bR_c$, and $NR_eR_f$.

Another specific value for $R^1$ is aryl or heteroaryl, wherein said aryl or heteroaryl is optionally substituted with halo, nitro, cyano, hydroxy, trifluoromethyl, trifluoromethoxy, $(C_1-C_{15})$alkyl, $(C_2-C_{15})$alkenyl, $(C_2-C_{15})$alkynyl, $(C_3-C_8)$cycloalkyl, $(C_3-C_8)$cycloalkyl$(C_1-C_{15})$alkyl, $(C_3-C_8)$cycloalkyl-$(C_2-C_{15})$alkenyl, $(C_3-C_8)$cycloalkyl$(C_2-C_{15})$alkynyl, $(C_1-C_{15})$alkoxy, $(C_1-C_{15})$alkanoyl, $(C_1-C_{15})$alkanoyloxy, $C(=O)OR_a$, $C(=O)NR_bR_c$, $OC(=O)OR_a$, $OC(=O)NR_bR_c$, and $NR_eR_f$.

Another specific value for $R^1$ is aryl wherein said aryl is optionally substituted with one or more (e.g. 1, 2, 3, or 4) substituents independently selected from the group consisting of halo, nitro, cyano, hydroxy, trifluoromethyl, trifluoromethoxy, $(C_1-C_{15})$alkyl, $(C_2-C_{15})$alkenyl, $(C_2-C_{15})$alkynyl, $(C_3-C_8)$cycloalkyl, $(C_3-C_8)$cycloalkyl$(C_1-C_{15})$alkyl, $(C_3-C_8)$cycloalkyl-$(C_2-C_{15})$alkenyl, $(C_3-C_8)$cycloalkyl$(C_2-C_{15})$alkynyl, $(C_1-C_{15})$alkoxy, $(C_1-C_{15})$alkanoyl, $(C_1-C_{15})$alkanoyloxy, $C(=O)OR_a$, $C(=O)NR_bR_c$, $OC(=O)OR_a$, $OC(=O)NR_bR_c$, and $NR_eR_f$.

Another specific value for $R^1$ is aryl wherein said aryl is optionally substituted with halo, nitro, cyano, hydroxy, trifluoromethyl, trifluoromethoxy, $(C_1-C_{15})$alkyl, $(C_2-C_{15})$alkenyl, $(C_2-C_{15})$alkynyl, $(C_3-C_8)$cycloalkyl, $(C_3-C_8)$cycloalkyl$(C_1-C_{15})$alkyl, $(C_3-C_8)$cycloalkyl-$(C_2-C_{15})$alkenyl, $(C_3-C_8)$cycloalkyl$(C_2-C_{15})$alkynyl, $(C_1-C_{15})$alkoxy, $(C_1-C_{15})$alkanoyl, $(C_1-C_{15})$alkanoyloxy, $C(=O)OR_a$, $C(=O)NR_bR_c$, $OC(=O)OR_a$, $OC(=O)NR_bR_c$, and $NR_eR_f$.

Another specific value for $R^1$ is aryl or heteroaryl wherein said aryl or heteroaryl is substituted with one or more (e.g. 1, 2, 3, or 4) substituents independently selected from the group consisting of halo, nitro, cyano, hydroxy, trifluoromethyl, trifluoromethoxy, $(C_3-C_8)$cycloalkyl, $(C_3-C_8)$cycloalkyl$(C_1-C_{15})$alkyl, $(C_3-C_8)$cycloalkyl$(C_2-C_{15})$alkenyl, $(C_3-C_8)$cycloalkyl$(C_2-C_{15})$alkynyl, $(C_1-C_{15})$alkoxy, $(C_1-C_{15})$alkanoyl, $(C_1-C_{15})$alkanoyloxy, $C(=O)OR_a$, $C(=O)NR_bR_c$, $OC(=O)OR_a$, $OC(=O)NR_bR_c$, and $NR_eR_f$.

Another specific value for $R^1$ is phenyl or naphthyl, wherein said phenyl or naphthyl is optionally substituted with one or more (e.g. 1, 2, 3, or 4) substituents independently selected from the group consisting of halo, nitro, cyano, hydroxy, trifluoromethyl, trifluoromethoxy, $(C_1-C_6)$alkyl, $(C_2-C_6)$alkenyl, $(C_2-C_6)$alkynyl, $(C_3-C_8)$cycloalkyl, $(C_3-C_8)$cycloalkyl$(C_1-C_6)$alkyl, $(C_3-C_8)$cycloalkyl$(C_1-C_6)$alkenyl, $(C_3-C_8)$cycloalkyl$(C_1-C_6)$alkynyl, $(C_1-C_6)$alkoxy, $(C_1-C_6)$alkanoyl, $(C_2-C_6)$alkanoyloxy, $C(=O)OR_a$, $C(=O)NR_bR_c$, $OC(=O)OR_a$, $OC(=O)NR_bR_c$, and $NR_eR_f$.

Another specific value for $R^1$ is phenyl or naphthyl, wherein said phenyl or naphthyl is optionally substituted with halo, nitro, cyano, hydroxy, trifluoromethyl, trifluoromethoxy, $(C_1-C_{15})$alkyl, $(C_2-C_{15})$alkenyl, $(C_2-C_{15})$alkynyl, $(C_3-C_8)$cycloalkyl, $(C_3-C_8)$cycloalkyl$(C_1-C_{15})$alkyl, $(C_3-C_8)$cycloalkyl-$(C_2-C_{15})$alkenyl, $(C_3-C_8)$cycloalkyl$(C_2-C_{15})$alkynyl, $(C_1-C_{15})$alkoxy, $(C_1-C_{15})$alkanoyl, $(C_1-C_{15})$alkanoyloxy, $C(=O)OR_a$, $C(=O)NR_bR_c$, $OC(=O)OR_a$, $OC(=O)NR_bR_c$, and $NR_eR_f$.

Another specific value for $R^1$ is aryl or heteroaryl, wherein said aryl or heteroaryl is substituted with $(C_1-C_{15})$alkyl, $(C_2-C_{15})$alkenyl, $(C_2-C_{15})$alkynyl, $(C_1-C_{15})$alkoxy, $(C_1-C_{15})$alkanoyl, or $(C_1-C_{15})$alkanoyloxy, and can also be optionally substituted with 1 or 2 halo, nitro, cyano, hydroxy, trifluoromethyl, trifluoromethoxy, $(C_1-C_6)$alkyl, $(C_3-C_8)$cycloalkyl, $(C_1-C_6)$alkoxy, $(C_1-C_6)$alkanoyl, $(C_2-C_6)$alkanoyloxy, $C(=O)OR_a$, $C(=O)NR_bR_c$, or $NR_eR_f$.

Another specific value for $R^1$ is phenyl or naphthyl, wherein said phenyl or naphthyl is substituted (preferably at the 4-position) with $(C_1-C_{15})$alkyl, $(C_2-C_{15})$alkenyl, $(C_2-C_{15})$alkynyl, $(C_1-C_{15})$alkoxy, $(C_1-C_{15})$alkanoyl, or $(C_1-C_{15})$alkanoyloxy, and can also be optionally substituted with 1 or 2 halo, nitro, cyano, hydroxy, trifluoromethyl, trifluoromethoxy, $(C_1-C_6)$alkyl, $(C_3-C_8)$cycloalkyl, $(C_1-C_6)$alkoxy, $(C_1-C_6)$alkanoyl, $(C_2-C_6)$alkanoyloxy, $C(=O)OR_a$, $C(=O)NR_bR_c$, or $NR_eR_f$.

A more specific value for $R^1$ is phenyl or naphthyl; optionally substituted with 1, 2, or 3 substituents independently selected from the group consisting of halo, nitro, cyano, hydroxy, trifluoromethyl, trifluoromethoxy, $(C_1-C_6)$alkyl, $(C_2-C_{10})$alkenyl, $(C_2-C_{10})$alkynyl $(C_3-C_8)$cycloalkyl, $(C_3-C_8)$cycloalkyl$(C_1-C_6)$alkyl, $(C_1-C_{10})$alkoxy, $(C_1-C_{10})$alkanoyl, $(C_2-C_{10})$alkanoyloxy, $C(=O)OR_a$, $C(=O)NR_bR_c$, or $NR_eR_f$;$R_a$ is hydrogen or $(C_1-C_6)$alkyl.

Another more specific value for $R^1$ is phenyl or naphthyl, wherein said phenyl or naphthyl is substituted (preferably at the 4-position) with $(C_1-C_{15})$alkyl, $(C_2-C_{15})$alkenyl, $(C_2-C_{15})$alkynyl, $(C_1-C_{15})$alkoxy, $(C_1-C_{15})$alkanoyl, or $(C_1-C_{15})$alkanoyloxy.

Another more specific value for $R^1$ is phenyl or naphthyl, wherein said phenyl or naphthyl is substituted (preferably at the 4-position with $(C_1-C_{15})$alkyl, $(C_2-C_{15})$alkenyl, or $(C_2-C_{15})$alkynyl.

Another more specific value for $R^1$ is phenyl substituted (preferably at the 4-position) with $(C_8-C_{15})$alkyl, $(C_8-C_{15})$alkenyl, $(C_8-C_{15})$alkynyl, $(C_8-C_{15})$alkoxy, $(C_8-C_{15})$alkanoyl, or $(C_8-C_{15})$alkanoyloxy.

Another more specific value for $R^1$ is aryl (e.g. phenyl, naphthyl, or 5, 6, 7, 8-tetrahydronaphthyl) substituted (preferably at the 4-position) with $(C_7-C_{10})$alkyl, $(C_7-C_{10})$alkenyl, $(C_7-C_{10})$alkynyl, $(C_7-C_{10})$alkoxy, $(C_7-C_{10})$alkanoyl, or $(C_7-C_{10})$alkanoyloxy.

Another more specific value for $R^1$ is naphthyl, optionally substituted (preferably at the 4-position) with $(C_1-C_{15})$alkyl, $(C_2-C_{15})$alkenyl, $(C_2-C_{15})$alkynyl, $(C_1-C_{15})$alkoxy, $(C_1-C_{15})$alkanoyl, or $(C_1-C_{15})$alkanoyloxy.

Another more specific value for $R^1$ is 5, 6, 7, 8-tetrahydronaphthyl, optionally substituted with $(C_1-C_{15})$ alkyl, $(C_2-C_{15})$alkenyl, $(C_2-C_{15})$alkynyl, $(C_1-C_{15})$alkoxy, $(C_1-C_{15})$alkanoyl, or $(C_1-C_{15})$alkanoyloxy, and optionally substituted at the 5, 6, 7, or 8 position with a divalent $(C_2-C_7)$alkylene chain to form a $(C_3-C_8)$spirocycloalkyl.

A preferred value for $R^1$ is 4-nonylphenyl, phenyl, 1-naphthyl, 4-hexanoyloxynaphth-1yl, 4-nonanoyloxy-naphth-1-yl, 4-(1-hexynyl)naphth-1-yl, 7,7-dimethyl-4-nonanoyloxy-5,6,7,8-tetrahydronaphth-1-yl, 4-nonanoyl-oxy-5,6,7,8-tetrahydronaphth-1-yl, 4-hexanoyloxy-5,6,7, 8tetrahydronaphth-1-yl, 4-nonanoyloxy-7-spirocyclopropyl-5,6,7,8-tetrahydronaphth-1-yl, or 3-pentyl.

A specific value for $R^2$ is $(C_1-C_{10})$alkyl, $(C_2-C_{10})$alkenyl, $(C_3-C_8)$cycloalkyl, $(C_3-C_8)$cycloalkyl$(C_1-C_6)$alkyl, $(C_1-C_{10})$alkoxy, $(C_1-C_{10})$alkanoyl, or $(C_1-C_{10})$alkanoyloxy, optionally substituted with 1, 2, or 3 substituents independently selected from the group consisting of halo, nitro, cyano, hydroxy, trifluoromethyl, trifluoromethoxy, $(C_1-C_6)$alkyl, $(C_2-C_{10})$alkenyl, $(C_2-C_{10})$alkynyl, $(C_3-C_8)$cycloalkyl, $(C_3-C_8)$cycloalkyl$(C_1-C_6)$alkyl, $(C_1-C_{10})$alkoxy, $(C_1-C_{10})$alkanoyl, $(C_2-C_{10})$alkanoyloxy, $C(=O)OR_a$, $C(=O)NR_bR_c$, or $NR_eR_f$.

Another specific value for $R^2$ is $(C_1-C_{10})$alkyl, $(C_2-C_{10})$alkenyl, $(C_3-C_8)$cycloalkyl, $(C_3-C_8)$cycloalkyl$(C_1-C_6)$alkyl, $(C_1-C_{10})$alkoxy, $(C_1-C_{10})$alkanoyl, or $(C_1-C_{10})$alkanoyloxy, optionally substituted with a substituent selected from the group consisting of halo, nitro, cyano, hydroxy, trifluoromethyl, trifluoromethoxy, $(C_1-C_6)$alkyl, $(C_2-C_{10})$alkenyl, $(C_2-C_{10})$alkynyl, $(C_3-C_8)$cycloalkyl, $(C_3-C_8)$cycloalkyl$(C_1-C_6)$alkyl, $(C_1-C_{10})$alkoxy, $(C_1-C_{10})$alkanoyl, $(C_2-C_{10})$alkanoyloxy, $C(=O)OR_a$, $C(=O)NR_bR_c$, or $NR_eR_f$.

Another specific value for $R^2$ is $(C_1-C_{10})$alkyl, optionally substituted with 1, 2, or 3 substituents independently selected from the group consisting of halo, nitro, cyano, hydroxy, trifluoromethyl, trifluoromethoxy, $(C_1-C_6)$alkyl, $(C_2-C_{10})$alkenyl, $(C_2-C_{10})$alkynyl, $(C_3-C_8)$cycloalkyl, $(C_3-C_8)$cycloalkyl$(C_1-C_6)$alkyl, $(C_1-C_{10})$alkoxy, $(C_1-C_{10})$alkanoyl, $(C_2-C_{10})$alkanoyloxy, $C(=O)OR_a$, $C(=O)NR_bR_c$, or $NR_eR_f$.

Another specific value for $R^2$ is $(C_1-C_{10})$alkyl, optionally substituted with a substituent selected from the group consisting of halo, nitro, cyano, hydroxy, trifluoromethyl, trifluoromethoxy, $(C_1-C_6)$alkyl, $(C_2-C_{10})$alkenyl, $(C_2-C_{10})$alkynyl, $(C_3-C_8)$cycloalkyl, $(C_3-C_8)$cycloalkyl$(C_1-C_6)$alkyl, $(C_1-C_{10})$alkoxy, $(C_1-C_{10})$alkanoyl, $(C_2-C_{10})$alkanoyloxy, $C(=O)OR_a$, $C(=O)NR_bR_c$, or $NR_eR_f$.

Another specific value for $R^2$ is $(C_1-C_{15})$alkyl, $(C_2-C_{15})$alkenyl, $(C_2-C_{15})$alkynyl, $(C_3-C_8)$cycloalkyl, $(C_3-C_8)$cycloalkyl$(C_1-C_{10})$alkyl, $(C_1-C_{15})$alkoxy, $(C_1-C_{15})$alkanoyl, $(C_1-C_{15})$alkanoyloxy, aryl, heteroaryl, aryl$(C_1-C_6)$alkyl, heteroaryl$(C_1-C_6)$alkyl, aryl$(C_2-C_{15})$alkenyl, heteroaryl$(C_2-C_{15})$alkenyl, aryl$(C_2-C_{15})$alkynyl, heteroaryl$(C_2-C_{15})$alkynyl, aryl $(C_1-C_{15})$alkoxy, heteroaryl $(C_1-C_{15})$alkoxy, aryl$(C_1-C_{15})$alkanoyl, heteroaryl$(C_1-C_{15})$alkanoyl, aryl$(C_1-C_{15})$alkanoyloxy, or heteroaryl$(C_1-C_{15})$alkanoyloxy; wherein said $R^2$ is optionally substituted with one or more (e.g. 1, 2, 3, or 4) substituents independently selected from the group consisting of halo, nitro, cyano, hydroxy, trifluoromethyl, trifluoromethoxy, $(C_1-C_6)$alkoxy, $(C_1-C_6)$alkanoyl, $(C_2-C_6)$alkanoyloxy, $C(=O)OR_a$, $C(=O)NR_bR_c$, and $NR_eR_f$.

Another specific value for $R^2$ is $(C_1-C_{15})$alkyl, $(C_2-C_{15})$alkenyl, $(C_2-C_{15})$alkynyl, $(C_3-C_8)$cycloalkyl, $(C_3-C_8)$cycloalkyl$(C_1-C_{10})$alkyl, $(C_1-C_{15})$alkoxy, $(C_1-C_{15})$alkanoyl, or $(C_2-C_{10})$alkanoyloxy; wherein said $R^2$ is optionally substituted with one or more (e.g. 1, 2, 3, or 4) substituents independently selected from the group consisting of halo, nitro, cyano, hydroxy, trifluoromethyl, trifluoromethoxy, $(C_1-C_6)$alkoxy, $(C_1-C_6)$alkanoyl, $(C_2-C_6)$alkanoyloxy, $C(=O)OR_a$, $C(=O)NR_bR_c$, and $NR_eR_f$.

Another specific value for $R^2$ is $(C_1-C_{15})$alkyl, $(C_2-C_{15})$alkenyl, or $(C_2-C_{15})$alkynyl, wherein said $R^2$ is substituted with one or more (e.g. 1, 2, 3, or 4) substituents independently selected from the group consisting of halo, nitro, cyano, hydroxy, trifluoromethyl, trifluoromethoxy, $(C_1-C_6)$alkoxy, $(C_1-C_6)$alkanoyl, $(C_2-C_6)$alkanoyloxy, $C(=O)OR_a$, $C(=O)NR_bR_c$, and $NR_eR_f$.

A more specific value for $R^2$ is $(C_1-C_{15})$alkyl, $(C_2-C_{15})$alkenyl, or $(C_2-C_{15})$alkynyl.

Another more specific value for $R^2$ is $(C_1-C_{15})$alkyl.

Another more specific value for $R^2$ is $(C_1-C_6)$alkyl.

Another more specific value for $r^2$ is $(C_3-C_6)$alkyl.

A preferred value for $R^2$ is isopropyl or 3-pentyl.

A preferred compound of formula I is (3R,4S, 5S)-3-isopropyl-4-(4-nonylphenyl)-5-(hydroxymethyl)pyrrolidin-2-one; (3R,4S, 5S)-3-isopropyl-4-phenyl-5-(hydroxymethyl)pyrrolidin-2-one; (3R,4S, 5S)-3-isopropyl-4-(1-naphthyl) -5-(hydroxymethyl)pyrrolidin-2-one; (3R, 4S, 5S)-3-isopropyl-4-(4-hexanoyloxynaphth-1-yl) -5-(hydroxymethyl)pyrrolidin-2-one; (3R,4S, 5S)-3-isopropyl-4-(4-nonanoyloxynaphth-1-yl) -5-(hydroxymethyl) pyrrolidin-2-one; or (3R,4S, 5S)-3-isopropyl-4-[4-(heptyn-1-yl)naphth-1-yl]-5-hydroxymethylpyrrolidin-2-one; or a pharmaceutically acceptable salt thereof.

A specific compound is a compound of formula I wherein $R^1$ is aryl; and $R^2$ is $(C_1-C_{10})$alkyl, $(C_2-C_{10})$alkenyl, $(C_3-C_8)$cycloalkyl, $(C_3-C_8)$cycloalkyl$(C_1-C_6)$alkyl, $(C_1-C_{10})$alkoxy, $(C_1-C_{10})$alkanoyl, or $(C_1-C_{10})$alkanoyloxy; or a pharmacuetically acceptable salt thereof.

A preferred compound is a compound of formula I wherein: $R^1$ is aryl, heteroaryl, aryl$(C_1-C_6)$alkyl, heteroaryl $(C_1-C_6)$alkyl, aryl$(C_2-C_6)$alkenyl, or heteroaryl$(C_2-C_6)$alkenyl; $R^2$ is $(C_1-C_{10})$alkyl, $(C_2-C_{10})$alkenyl, $(C_3-C_8)$cycloalkyl, $(C_3-C_8)$cycloalkyl$(C_1-C_6)$alkyl, $(C_1-C_{10})$alkoxy, $(C_1-C_{10})$alkanoyl, $(C_1-C_{10})$alkanoyloxy; aryl, heteroaryl, aryl$(C_1-C_6)$alkyl, or heteroaryl$(C_1-C_6)$alkyl; wherein any $R^1$ or $R^2$ is optionally substituted with 1, 2, or 3 substituents independently selected from the group consisting of halo, nitro, cyano, hydroxy, trifluoromethyl, trifluoromethoxy, $(C_1-C_6)$alkyl, $(C_2-C_{10})$alkenyl, $(C_2-C_{10})$alkynyl, $(C_3-C_8)$cycloalkyl, $(C_3-C_8)$cycloalkyl$(C_1-C_6)$alkyl, $(C_1-C_{10})$alkoxy, $(C_1-C_{10})$alkanoyl, $(C_2-C_{10})$alkanoyloxy, $C(=O)OR_a$, $C(=O)NR_bR_c$, or $NR_eR_f$; $R_a$ is hydrogen or $(C_1-C_6)$alkyl; $R_b$ and $R_c$ are each independently hydrogen or $(C_1-C_{10})$ alkyl; or $R_b$ and $R_c$ together with the nitrogen to which they are attached are a 5–6 membered heterocyclic ring, i.e. a pyrrolidino, piperidino or morpholino ring; and $R_e$ and $R_f$ are each independently hydrogen, $(C_1-C_{10})$alkyl, $(C_1-C_{10})$alkanoyl, phenyl, benzyl, or phenethyl; or $R_e$ and $R_f$ together with the nitrogen to which they are attached are a 5–6 membered heterocyclic ring, i.e. a pyrrolidino, piperidino or morpholino ring; or a pharmaceutically acceptable salt thereof.

A preferred compound is a compound of formula I wherein $R^1$ is optionally substituted phenyl or naphthyl and $R^2$ is isopropyl; or a pharmaceutically acceptable salt thereof.

Processes for preparing compounds of formula I are provided as further embodiments of the invention and are illustrated by the following procedures in which the meanings of the generic radicals are as given above unless otherwise qualified. Compounds of formula I can be prepared from a corresponding compound of formula I wherein the pyrrolidinone nitrogen bears a suitable nitrogen protecting group by deprotection of the nitrogen. For example, a compound of formula I can be prepared by deprotection of a corresponding tert-butoxycarbonyl (BOC) protected pyrrolidinone using conditions similar to those described in Example 1. Suitable nitrogen protecting groups are well known in the art (See Greene, T. W.; Wutz, P. G. M. "Protecting Groups In Organic Synthesis" second edition, 1991, New York, John Wiley & sons, Inc.).

Compounds of formula I can be prepared from a corresponding compound wherein the hydroxymethyl of formula I bears a suitable hydroxyl protecting group, by deprotection of the hydroxyl group. For example, a compound of formula I can be prepared by deprotection of a corresponding tert-butyldimethylsilyl (TBS) protected alcohol using conditions similar to those described in Example 1. Suitable hydroxyl protecting groups are well known in the art (See Greene, T. W.; Wutz, P. G. M. "Protecting Groups In Organic Synthesis" second edition, 1991, New York, John Wiley & sons, Inc.).

Compounds of formula I can be prepared from a corresponding acetonide or formula II:

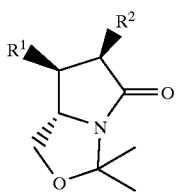

(II)

wherein $R^1$ and $R^2$ have any of the values defined herein for $R^1$ and $R^2$, respectively, in a compound of formula I, by removal of the acetonide using procedures which are well known in the art. For example a compound of formula I can be prepared from an acetonide of formula II using a procedure similar to that described in Example 6.

A convenient intermediate for the preparation of compounds of the invention is an acetonide of formula II. An intermediate of formula II may conveniently be prepared using a synthetic scheme similar to that illustrated in FIG. 1. Acylation of D-serine methyl ester hydrochloride with bromo-isovaleryl chloride followed by protection of the free hydroxyl and amido group with 2,2-dimethoxypropane in the presence of catalytic amounts of acid gives a compound of formula (6). Selective reduction of the methyl ester with DIBAL at −70° C. gives an aldehyde, which can be treated with a Grignard reagent ($R^1$MgBr). The resulting secondary alcohol can be oxidized with NMO, 4 Å molecular sieves and a catalytic amount of tetrapropylammonium perruthenate (TPAP) to give a ketone of formula 7a. $SmI_2$ mediated Reformatsky-type reaction gives the pyrrolidinone (8) with the absolute and relative stereochemistry depicted. The tertiary alcohol can be removed using a Barton reaction to give an intermediate of formula II having the expected cis-C3'/C4' configuration.

The Barton reaction on intermediate reaction on intermediate 8b, may not give the product of reversed C-4 configuration with removal of the hydroxyl group in high yield. However, as illustrated in FIG. 1, fluorination of the tertiary alcohol, with diethylaminosulfur trifluoride (DAST) gives compound 9, possessing the naphthyl and isopropyl groups in a cis relationship. Treatment of 9b with 5% Pd/C in methanol under hydrogen, gives the debenzylated/defluorinated compound 10b, which is a compound of formula II that can be acylated or alkylated to give compounds of the invention.

Figure 2:
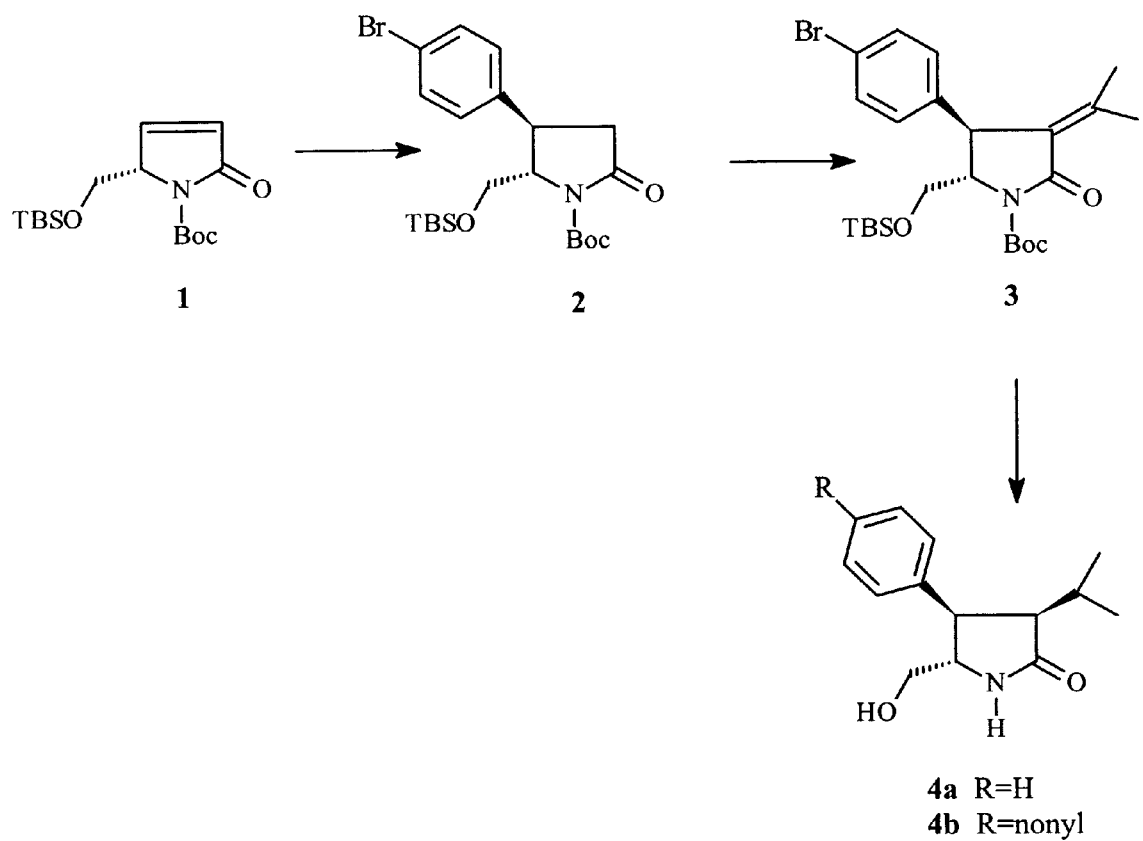

Compounds of the invention may also be prepared using procedures similar to those described in the Examples herein. As illustrated in FIG. 2, a suitably protected compound (1) can be prepared from L-glutamic acid using procedures which are well known in the art. Conjugate addition of a cuprate in the presence of TMSCl and HMPA introduces a substituent $R^1$ (4-bromophenyl as shown in FIG. 2) to give compound 2. Aldol condensation with acetone gives a tertiary alcohol, which can be dehydrated using Burgess reagent to form a mixture of endo- and exocyclic olefins. Isomerization of the endocyclic olefin under basic condition gives a lactam 3. Removal of the silyl group with TBAF, followed by hydroxyl directed heterogeneous catalytic hydrogenation of the double bond over 10% Pd/C gives a compound with the requisite C3'/C4cis relative stereochemistry. Deprotection of the pyrrolidone nitrogen with trifluoroacetic acid in anhydrous methylene chloride at room temperature gives compound (4a), which is a compound of the invention. Compounds of the invention wherein $R^1$ is aryl substituted with an alkynyl substituent (for example compound (4b) can be prepared by including a palladium-catalyzed coupling reaction with the requsite alkyne in the above synthetic sequence. For example, as shown in Example 1, sub-part d.

Figure 4:
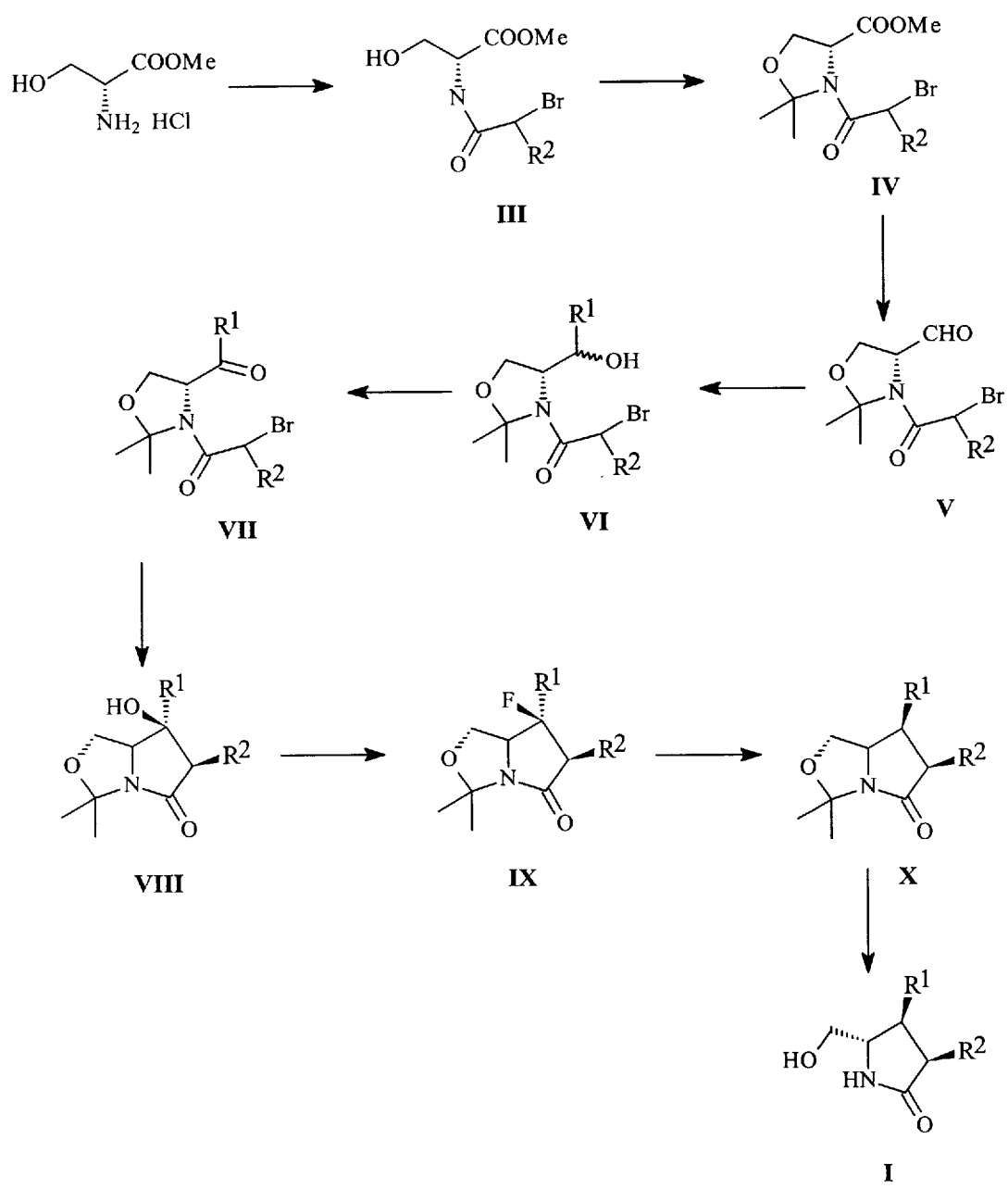
Figure 5:
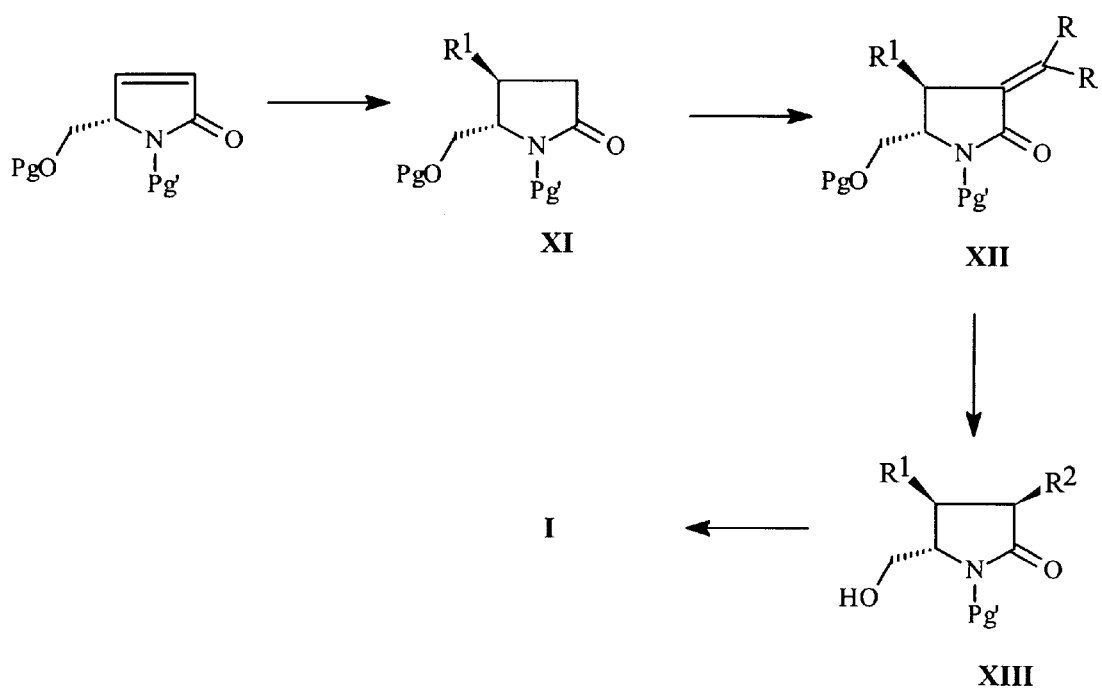

Compounds of formula I can also be prepared using the general synthetic schemes outlined in FIGS. 4 and 5. Accordingly, the invention also provides an intermediate of formula III, IV, V, VI, VII, VIII, IX, X, XI, XII, or XIII, wherein $R^1$ and $R^2$ have any of the values, specific values, more specific values, or preferred values defined herein for a the corresponding radical in a compound of formula I, as well as methods for the preparation of these intermediates. As shown in formulae XI and XII, Pg represents a suitable hydroxy protecting group and Pg' represents a suitable nitrogen protecting group. Suitable hydroxy and nitrogen protecting groups are well known in the art (See Greene, T. W.; Wutz, P. G. M. "Protecting Groups In Organic Synthesis" second edition, 1991, New York, John Wiley & sons, Inc.).

Figure 6:
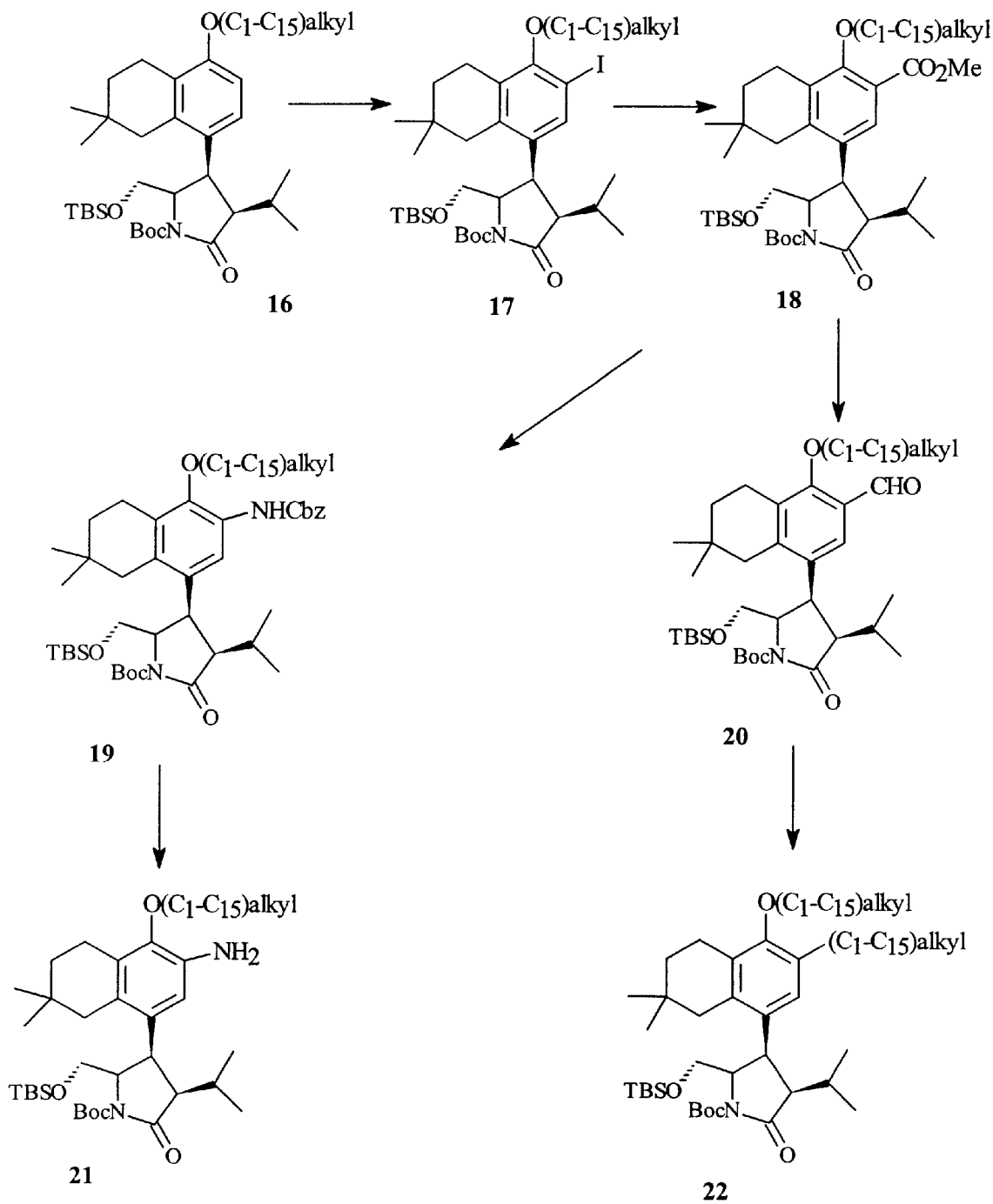

Additionally, compounds of Formula I can be prepared using methods similar to those illustrated in FIG. 6. An intermediate of formula 16 can be prepared by alkylation of a compound of formula 13 (FIG. 3) using standard conditions. Compound 16 can be iodinated with sodium iodide and tert-butyl hypochlorite to give a compound of formula 17, which can be converted to a compound of formula I by removal of the hydroxy and nitrogen protecting groups. An iodo compound of formula 17, can be converted to the corresponding ester of formula 18 by treatment with carbon monoxide in methanol, in the presence of triethylamine and catalytic Pd(OAc)$_2$/PPh$_3$. Reduction of the ester 18 gives the corresponding alcohol, which can be oxidized under Swern conditions to give an aldehyde of formula 20. Wittig reaction of a compound of formula 20, followed by reduction of the resulting double bond, yields a compound of formula 22.

An ester intermediate of formula 18, can also be converted to a protected amine formula 19 by hydrolysis of the ester followed by Curtius rearrangement with (PhO)$_2$P(O)N$_3$ and benzyl alcohol. The corresponding amine of formula 21 can then be prepared by removal of the Cbz group.

Compounds of formulae 16–18 and 20–22 can be converted to compounds of formula I by removal of the TBS and Boc protecting groups under standard conditions.

In cases where compounds of formula I are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds of formula I can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its slats can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form must be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monosterate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are disclosed in Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compound(s) of formula I in a liquid composition, such as a lotion, will be from about 0.1–25 wt-%, preferably from about 0.5–10 wt-%. The concentration in a semi-solid or solid composition such as a gel or a powder will be about 0.1–5 wt-%, preferably about 0.5–2.5 wt-%. Single dosages for injection, infusion or ingestion will generally vary between 50–1500 mg, and may be administered, i.e., 1–3 times daily, to yield levels of about 0.5–50 mg/kg, for adults.

Accordingly, the invention includes a pharmaceutical composition comprising a compound of formula I as described herinabove; or a pharmaceutically acceptable salt thereof, in combination with a pharmaceutically acceptable carrier. Pharmaceutical compositions adapted for oral, topical or parenteral administration, comprising an amount of one or more compounds of formula (I) effective to treat mammalian conditions associated with pathological cellular proliferation, particularly human cancers, such as solid tumors and leukemias, are a preferred embodiment of the invention.

The ability of a compound of the invention to activate PKC can be demonstrated using the pharmacological models described herein, or using other pharmacological models which are known in the art.

The ability of representative compounds of the invention to activate PKC was determined using a procedure similar to that described in A. Kozikowski et al. *J. Med. Chem.*, 1997, 4, 1316–1326. Results are shown in Table 1.

TABLE 1

|  | 4a | 4b | 11a | 11b | 11c | 11d |
|---|---|---|---|---|---|---|
| Ki ± SEM | 129 ± 13 μM | 2.3 ± 0.2 μM | 5.5 ± 0.9 μM | 0.5 ± 0.04 μM | 0.3 ± 0.01 μM | 1.5 ± 0.2 μM |

Because of their ability to activate PKC, compounds of the invention may be useful for treating diseases or conditions wherein PKC activity is implicated and wherein activation of PKC is desirable. For example, compounds of the invention may be useful for treating a disease or condition characterized by the pathological proliferation of mammalian cells, such as for example, human cancers, such as solid tumors and leukemias. Compounds of the invention may also be useful for treating autoimmune diseases, and inflammation.

Accordingly, the invention includes a method comprising modulating PKC in a mammal by administering to said mammal a pharmaceutically effective dose of a compound of formula I; or a pharmaceutically acceptable salt thereof. The invention also provides a method comprising treating a condition characterized by the pathological proliferation of mammalian cells by administering to a mammal afflicted with such a condition, an effective amount of a compound of formula I; or a pharmaceutically acceptable salt thereof.

The invention will now be illustrated by the following non-limiting examples in which unless otherwise stated: NMR spectra were acquired at proton frequencies of 300 MHz, using $CDCl_3$ as solvent unless noted otherwise. $^1H$ chemical shifts were reported with $Me_4Si$ (δ=0.00 ppm) or $CHCl_3$ (δ=7.26 ppm) as internal standards and $^{13}C$ chemical shifts with $CHCl_3$ (δ=77.00 ppm) or TMS (δ=0.00 ppm) as internal standards. Mass spectra were obtained in electron impact ionization mode at 70 eV. Optical rotations were measured at room temperature.

EXAMPLES

Example 1
(3R, 4S, 5S)-3-Isopropyl-4-(4-nonylphenyl)-5-(hydroxymethyl)-pyrrolidin-2-one (4b):

100 μl or $CF_3COOH$ was added to the solution of 8 mg of the compound from sub-part e (17.4 mol) in 1 ml of anhydrous dichloromethane. After 15 minutes, the solution was poured into cold sat. aq. $NaHCO_3$ and extracted with dichloromethane. After concentration, the final product was purified by TLC giving 5.8 mg (93.5%); IR (film): 3300, 2956,1691 $cm^{-1}$;$[α]_D$=+5.59° (c=0.84 in $CHCl_3$); $^1HNMR$ ($CDCl_3$): δ 7.14 (br.s, 4H), 6.68 (s, 1H, OH), 3.74 (br.d, 1H, J=11.1 Hz), 3.64 (td, 1H), J=7.5, 2.4 Hz), 3.47 (dd, 1H, J=10.5, 7.5 Hz), 3.00 (br.t, 1H), J=9.0 Hz), 2.72 (br.dd, 2H, 2H, J=11.2, 3.6 Hz), 2.58 (t, 2H, J=7.5 Hz), 2.21 (m, 1H), 1.60 (br.t, 2H), J=6.9 Hz), 1.26 (br.s, 12H), 0.97 (d, 3H, J=6.6 Hz), 0.88 (t, 3H, J=6.3 Hz), 0.79(d, 3H), J=6.9 Hz); $^{13}C$ NMR ($CDCl_3$): δ 178.10, 141.91, 138.93, 128.84×2, 127.74×2, 64.37, 62.33, 54.94, 44.32, 35.54, 31.88, 31.40, 29.54, 29.49, 29.35, 29.31, 27.70, 22.67, 19.97, 18.58, 14.11; MS: 359($M^+$, 0.96), 328,286,159,145,117,57, 44(100). Anal. for $C_{23}H_{37}NO_2$ Calcd. C, 76.83 H, 10.37 N, 3.90 Found C, 76.77 H, 10.49 N, 3.91

The intermediate was prepared as follows:

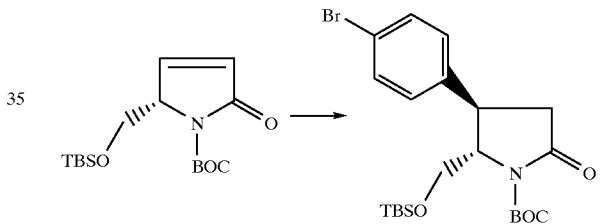

To a mixture of 19 mg of CuI (0.1 mmol) and 1 ml of $Me_2S$ in 10 ml of THF under nitrogen, was added 4-bromophenylmagnesium bromide ( 3.08 mmol). After stirring for 20 minutes, 91 μl of HMPA (5.1 mmol) and 610 μl of TMSCl (4.8 mmol) were added. The reaction mixture ws stirred for another 10 minutes followed by addition of the unsaturated lactam (1.85 mmol) in 10 ml of anhyudrous THF at −20° C. Stirring was continued for 3 hours at −20°) C. to 0° C., then the mixture was poured into cold sat. aq. $NH_4Cl$ and extracted with ether. After concentration, the product was purified by flash chromatography on silica gel ( Hexane/Ethyl acetate=15/1) giving 623 mg of an oil (70%);IR(film): 1789, 1752, 1714, 1310, 1154, 836, 778 $cm^{-1}$; m.p. 92–93° C.; $[α]_D$=20.2° (c=0.92 in $CHCl_3$); $^1HNMR$ ($CDCl_3$): δ 7.46 (br.s, 2H, J=8.4 Hz, 2Ar-H), 7.07 (d, 2H, J=8.4 Hz, 2Ar-H), 4.02 (m, 1H, C<u>H</u>N), 3.99 (dd, 1H, J=10.5, 3.9 Hz, OCH), 3.80 (dd, 1H, J=10.5, 1.5 Hz, OCH), 3.42(d, 1H, J=9.6 Hz, ArC<u>H</u>), 3.16 (dd, 1H, J=17.4, 9.6 Hz, CHC(O)), 2.48 (dd, 1H, J=17.4, 2.4 Hz, CHC(O)), 1.53 (s, 9H, t-Bu of Boc), 0.91 (s, 9H, t-Bu-Si, 0.08, 0.07(two s, 3H each, 2MeSi); $^{13}C$ NMR ($CDCl_3$): δ 173.70, 149.80, 143.23, 132.14×2, 128.08×2, 120.93, 83.28, 66.55, 63.60, 39.80, 38.30, 28.06×3, 25.82×3, 18.18, −5.51×2; MS: 412($M^+$1-BuO, 248), 328, 326, 57(100). Anal. for $C_{22}H_{35}BrNO_4Si$ Calcd. C, 54.54H, 7.07 N, 2.89 Found C, 54.93 H, 7.23 N, 2.88.

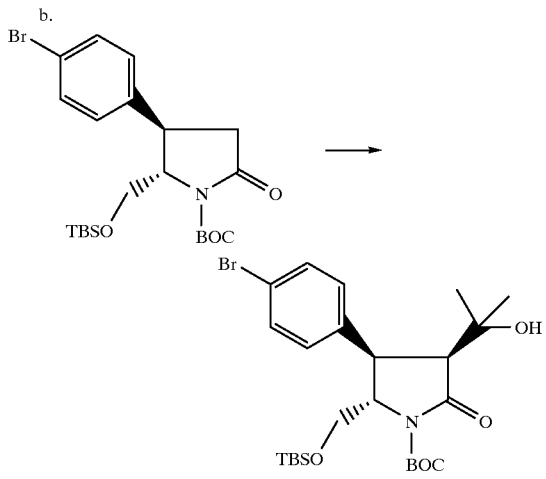

To a suspension of 88 mg of anhydrous (Mg(ClO₄)₂ (1.0 mmol) in 3 ml THF and 633 μl of hexamethyldisilazane (HMDSA) (3 mmol) under nitrogen, was added n-BuLi (1.20 ml. 3.0 mmol) at −78° C. After 20 minutes, the BOC protected pyrrolidinone 2 (0.455 mmol) in 4 ml of THF was added. After stirring for another hour at −78° C., 500 μl of anhydrous acetone (5 mmol) was added. The mixture was stirred for 5 hours at −78° C., poured into ice-water, extracted with ether and dried over MgSO₄. Evaporation and chromatography on silica gel afforded 178 mg of the tertiary alcohol (72%) as white syrup and 30 mg of starting material (14%); IR(film): 3483, 2930, 2780, 1780, 1724, 1304, 1155, 836, 778 cm⁻¹; [α]$_D$−5.39° (c=0.69 in CHCl₃); ¹H NMR (CDCl₃): δ 7.49 (d, 2H, J=8.4 Hz, 2Ar-H), 7.14 (d, 2H, J=8.4 Hz, 2Ar-H), 4.62(s, 1H, OH), 4.15(dd, 1H, J=10.8, 3.0 Hz), 3.75 (br.dd, 1H, J=9.1, 1.2 Hz), 3.48 (dd, 1H, J=10.8, 1.2 Hz), 3.33 (dd, 1H, J=10.8, 8.4 Hz), 2.95 (d, 1H, J=10.8 Hz), 1.55 (s, 9H, t-Bu of Boc), 0.90 (s, 9H, t-Bu-Si), 0.06, 0.04(two s, 3H each, 2MeSi); ¹³C NMR (CDCl₃): δ 175.60, 149.67, 140.73, 132.23×2, 129.81×2, 121.34m 83.79, 72.31, 65.22, 59.14, 58.76, 40.89, 28.54, 28.07×3, 25.81×3, 25.14, 18.24, −5.41, −5.47;

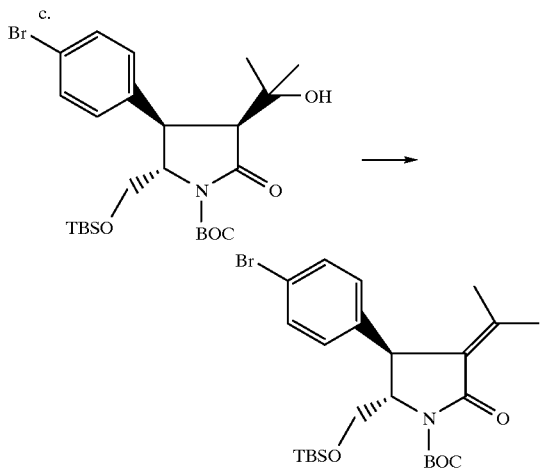

To 241 mg of the tertiary alcohol (0.445 mmol) in 3 ml of anhydrous benzene under nitrogen, was added 423 mg of Burgess reagent (4 eq.). The resulting solution was stirred at 60° C. for 2 hours, then filtered through a short silica gel column giving 226.8 mg (97.4%) of the eliminated products (two geometric isomers) as a colorless oil. Isomerization was achieved under basic condition by refluxing the mixture with 5 drops of DBU in toluene for two hours. The alkane (216 mg, 93% over two steps) was obtained by flash column chromatography on silica gel (Ethyl acetate/Hexane 1/15; IR(film): 1776, 1731, 1709, 1657, 1309, 1156, 837, 777 cm⁻¹; m.p. 109–110° C.; [α]$_D$=−70.48° (c=1.36 in CHCl₃); ¹HNMR (CDCl₃): δ 7.43 (d, 2H, J=8.4 Hz, 2Ar-H), 7.05 (d, 2H, J=8.4 Hz, 2Ar-H), 3.98 (br.s, 1H,), 3.85 (m, 2H,), 3.68 (dd, 1H, J=10.8, 6.6 Hz), 2.33 (s, 3H, vinyl Me), 1.66 (s, 3H, vinyl Me), 1.51 (s, 9H, t-Bu of Boc), 0.89 (s, 9H, t-Bu-Si), 0.06, 0.05 (two s, 3H each, 2MeSi), ¹³C NMR (CDCl₃): δ 166.70, 151.51, 150.74, 142.41, 131.92×2, 128.68×2, 126.88, 120.60, 82.75 64.05, 63.81, 43.82, 28.10×3, 25.69×3, 24.18, 20.33, 18.05, −5.43, −5.57; MS: 425(M⁺1-BuO, 1.64), 412, 410, 368, 366, 280, 128, 57(100). Anal. for C₂₅H₃₈BrNO₄Si Calcd. C, 57.24 H, 7.30 N, 2.67 Found C, 57.55 H, 7.15 N, 2.66

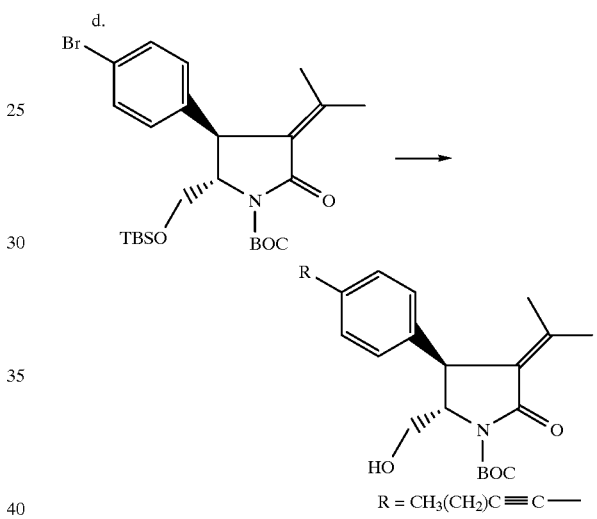

To a mixture of the alkelene from sub-part c (189 mg, 0.36 mmol), PdCl₂(PPh₃)₂ (26 mg, 0.036 mmol and Et₃N (1 ml) under argon, wee added 1-nonyne and CuI (4 mg, 0.02 mmol). The solution turned dark at once. After stirring at 80° C. for 3 hours, the resulting mixture was purified by flash chromatography eluting with ethyl acetate-hexanes (1/30) to afford 173.5 mg (85%). Desilylation was achieved by stirring with 0.5 ml of TBAF in 2 ml of THF for 1.5 hours. Then 10 ml water was added, and the mixture was extracted with ethyl acetate (2×20 ml) and dried over Na₂SO₄. Evaporation and column chromatography afforded primary alcohol (69.2 mg, 96%); IR(film): 3300, 2243(W), 1745, 1694, 1659, 1273, 1253, 860, 792, 760 cm⁻¹;[α]$_D$=−36.45° (c=1.1 in CHCl₃); ¹H NMR(CDCl₃): δ 7.33 (d, 2H, J=8.1 Hz, 2Ar-H), 7.10 (d, 2H, J=8.1 Hz, 2Ar-H), 6.13 (s, 1H, OH), 4.13 (dd, 1H, J=10.5, 5.4 Hz), 3.99 (dd, 1H, J=10.5, 7.8 Hz), 3.80 (br.s, 1H), 3.57 (br.t, 1H, J=5.4 Hz), 2.39 (t, 2H, J=6.9 Hz), 2.31 (s, 3H, vinyl Me), 1.56 (s, 3H, vinyl Me), 1.48 (s, 9H, t-Bu of BOC), 1.44(m, 2H), 1.30 (br.s, 6H, 3CH2), 0.89 (br.t, 3H, J=6.9 Hz, Me); ¹³C NMR (CDCl₃): δ 170.95, 153.11, 148.24, 142.39, 132.09×2, 126.81×2, 125.25, 122.77, 90.70, 82.80, 80.07, 69.15, 57.95, 47.02, 31.73, 28.86, 28.82, 28.72, 27.68×3, 23.94, 22.61, 19.72, 19.38, 14.08; MS: 453(M⁺, 0.46), 397, 322, 165, 141, 57, 44(100)

e.

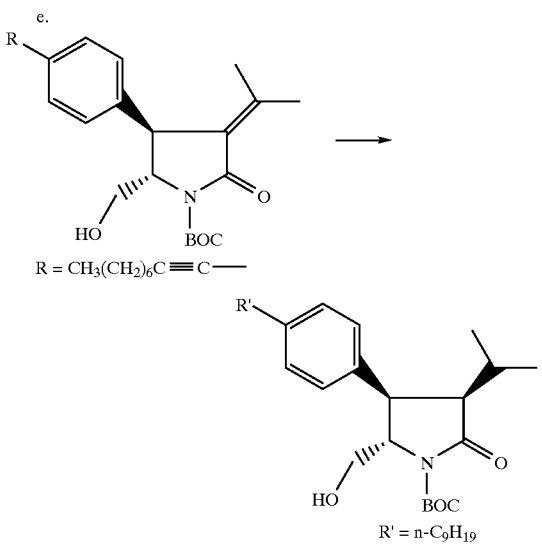

R = CH₃(CH₂)₆C≡C—

R' = n-C₉H₁₉

20 mg of the primary alcohol (0.044 mmol) was hydrogenated in 2 ml of ethanol over 5 mg of 10% Pd/C overnight. After filtration and concentration, the isopropyl product was obtained (21 mg, 100%); IR(film): 3300, 1956, 1744, 1702, 1369, 1277, 859 cm$^{-1}$; m.p. 55–56° C.;[α]$_D$=+24.60° (c=0.62 in CHCl₃); $^1$H NMR(CDCl₃): δ 7.14 (s, 4H), 5.91 (br.s, 1H, OH), 4.21 (dd, 1H, J=10.8, 2.4 Hz), 3.86 (dd, 1H, J=10.8, 7.8 Hz), 3.73 (dr, 1H, J=7.8, 2.4 Hz), 2.97 (t, 1H, J=8.4 Hz), 2.68 (dd, 1H, J=9.9, 3.3 Hz), 2.58 (t, 2H, J=7.8 Hz), 2.22 (m, 1H), 1.59 (m, 2H), 1.46 (s, 9H, t-Bu), 1.30–1.26 (m, 12H), 0.98 (d, 3H, J=6.9 Hz), 0.88 (t, 3H, J=6.9 Hz), 0.79 (d, 3H, J=6.9 Hz); $^{13}$C NMR (CDCl₃): δ 177.00, 153.22, 142.16, 138.17, 128.94×2, 127.69×2, 127.69×2, 82.81, 68.04, 59.15, 54.50, 44.90, 53.53, 31.87, 31.37, 29.51, 29.47, 29.33, 29.29, 27.65×4, 22.66, 19.84, 18.55, 14.10; MS: 459(M$^+$, 0.58), 444, 360, 341, 328, 272, 145, 57, 43(100). Anal. for C₂₈H₄₅NO₄ Calcd. C, 73.16 H, 9.87 N, 3.05 Found C, 73.17 H, 9.66 N, 3.06.

The requisite starting material for sub-part a may conveniently be prepared from L-glutamic acid using procedures which are well known in the art.

EXAMPLE 2

(3R, 4S, 5S)-3-Isopropyl-4-phenyl-5-(hydroxymethyl)pyrrolidin-2-one (4a):

Using a procedure similar to that described in Example 1 and the sub-parts thereof, except replacing the 4-bromophenylmagnesium bromide used in sub-part a with phenylmagnesium bromide, the title compound was prepared; $^1$HNMOR (CDCl₃): δ 7.26–7.34 (m, 5H), 6.63 (br.s, 1H, OH), 3.75 (br.d, 1H, J=10.8 Hz), 3.67 (td, 1H, J=7.5, 2.7 Hz), 3.49 (br.dd, J=10.8 5.7 Hz), 3.05 (dd 1H, J=9.9, 8.4 Hz), 2.75 (dd, 1H, J=9.9, 3.6 hz), 2.61 (br.s, 1H, NH), 2.23 (m, 1H), 0.98 (d, 3H, J=6.6 Hz), 0.89 (d, 3H, J=6.6 Hz); $^{13}$C NMR (CDCl₃): δ 177.85, 133.92, 132.65, 129.12, 127.8, 126.67, 122.89, 76.58, 65.29, 58.41, 51.54, 42.77, 27.06, 22.37, 18.57; MS m/z 283 (M$^+$35.0%), 252 (100%), 210 (76.5%), 43 (83.0%).

EXAMPLE 3

(3R,4S,5S)-3-Isopropyl-4-(1-naphthyl)-5-(hydroxymethyl)pyrrolidin-2-one (11a).

Using a procedure similar to that described in Example 6, the requisite acetonide from sub-part g was cleaved to give the title compound;;[α]$_D$=+282.4° ( c=0.15 in CHCl₃); IR: 3360, 1682, 1070 cm$^{-1}$; $^1$H NMR(CDCl₃): δ 7.98(d, 1H), 7.9(br.d, 1H), 7.81 (d, 1H), 7.44–7.60 (m, 4H), 6.70 (br.s, 1H), 4.47 (td, 1H), 4.21 (t, 1H), 3.90 (m, 1H), 3.60 (m, 1H), 2.97 (dd, 1H), 2.61 (br.t, 1H), 1.36 (m, 1H), 0.87 (d, 3H), 0.83 (d, 3H).

a.

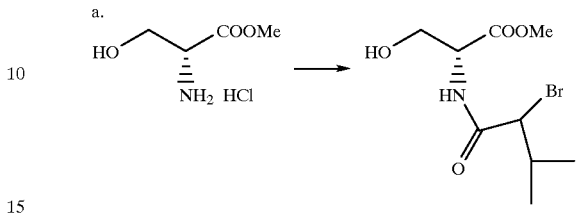

To the suspension of 4.67 g (30 mmol) of D-serine methyl ester hydrochloride in 150 mL of chloroform, was added 8.4 mL of Et₃N (60 mmol). After 10 minutes, 6.0 g (30 mmol) bromoisovaleryl chloride was added dropwise. The reaction mixture was stirred vigorously at room temperature for another 36 hours and washed with 50 mL of H₂O followed by 50 mL of brine. The solution was dried over anhydrous MgSO₄, then evaporated under reduced pressure. 6.77 g of the hydroxyamide (80% yield) was obtained after column chromatography on silica gel eluting with ethyl acetate-hexane (V/V=1/1) as a white solid. Anal. Calcd for C₉H₁₆BrNO₄ (282.13): C, 38.31; H, 5.72; N, 4.96. Found: C, 38.23; H, 5.66; N, 5.09.

b.

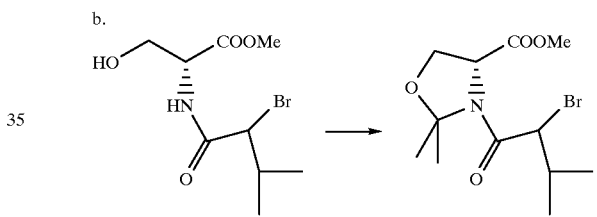

A solution of 7.15 g of the hydroxy amide (25.3 mmol), 7 mL of dimethoxypropane, (DMP) and 70 mg of p-toluenesulfonic acid (TsOH) in 70 mL of benzene was refluxed for 30 minutes. The benzene was distilled off slowly to a final volume of 20 mL another 2 mL of DMP and 50 mL of benzene were added, and the mixture was refluxed for 1 hour. TLC showed that almost no starting material was left by this time. Then the reaction mixture was refluxed through a soxhlet extractor filled with 4 Å molecular sieves, and the reaction was monitored by TLC. The resulting solution was cooled, washed with aqueous saturated NaHCO₃, and dried over MgSO₄. After concentration, the residue was purified by chromatography on silica gel (ethyl acetate/hexane=2/7) giving the acetonide as a yellow oil (4.06 g, 50%); IR: 2976, 1752, 1660, 1413, 1204, 839 cm$^{-1}$; $^1$H NMR (CDCl₃) δ 4.81 (dd, 1H of md, J=6.6, 3.3 Hz, CHBrC(O)), 4.51 (dd, 1H of MD, J=6.0, 4.2 Hz, CHBrC(O)), 4.28–4.06 (m, 2H+1H of md, OCH₂+NCH), 3.89 (d, 1H of MD, J=9.3 Hz, NCH), 3.84 (s, 3H of MD, OMe), 3.76 (s, 3H of md, OMe), 2.43 (m, 1H of md, CHMe₂), 2.26 (m, 1H of MD, CHMe₂), 1.76 (br.s, 3H, Me), 1.70 (s, 3H of md, Me), 1.59 (s, 3H of MD, Me), 1.20 (d, 3H of md, J=6.6 Hz, Me), 1.18 (d, 3H of MD, J=2.2 Hz, Me), 1.08 (s, 3H of md, J=6.6 Hz, Me), 1.01 (s, 3H of MD, J=6.6 Hz, Me); $^{13}$C NMR (CDCl₃) (major diastereoisomer) δ 170.05, 165.95, 97.33, 66.92, 59.48, 54.25, 52.98, 33.06, 24.52, 23.14, 20.51, 19.54; MS m/z 308/306 (M$^+$-Me, 5/5%), 144 (100%), 100 (37.5%). Anal. Calcd for C$_{12}$H$_{20}$BrNO$_4$ (322.20): C, 44.73; H, 6.26; N, 4.35. Found: C, 44.59; H, 6.32; N, 4.31.

c.

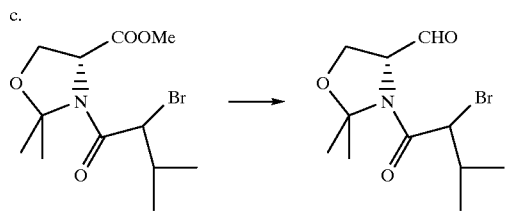

Under nitrogen, 11 mL of 1.0 mL DIBAL in hexanes was added dropwise to a solution of 2.75 g of the methyl ester (8.54 mmol) in 60 ml of anhydrous (CH$_2$Cl$_2$ with dry-ice/ acetone cooling to maintaining the internal temperature below −70° C. The resulting solution was stirred at −78° C. for 1.5 hours followed by slow addition 5 mL of methanol. After stirring at −70° C. for another 30 minutes, the solution was poured into 50 mL of 1N aqueous hydrochloric acid, and the mixture was extracted with 100 mL of dichloromethane. The organic layer was washed with 30 mL of brine and dried over MgSO$_4$. After concentration, the residue was purified by column chromatography eluting with ethyl acetate-hexane(V/V=2/5) to give 2.17 g of the aldehyde (87%).

d.

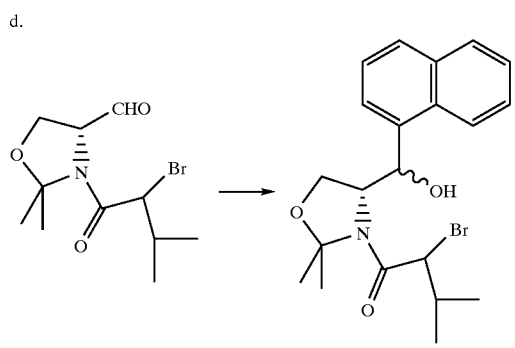

α-Naphthyl magnesium bromide was prepared from 1.55 g 1-bromonaphthalene (7.5 mmol) with 180 mg of magnesium in anhydrous THF. To the solution of 730 mg of aldehyde (2.5 mmol) in 20 mL of THF under nitrogen at −78° C. was added the Grignard reagent. After stirring at −78° C. for 30 minutes, the reaction mixture was warmed slowly to 0° C. and reacted at 0° C. for another 20 minutes followed by addition of 10 mL of 1N aq.HCl. 70 mL of ether was added, and the combined organic layers were washed with water, aq. NaHCO$_3$, and brine (30 ml each) and dried over MgSO$_4$. After concentration, the crude secondary alcohol mixture (780 mg, 74%) was obtained by flash column chromatography on silica gel with ethyl acetate-hexane (V/V=1/7 to 1/5) as a white foam.

e.

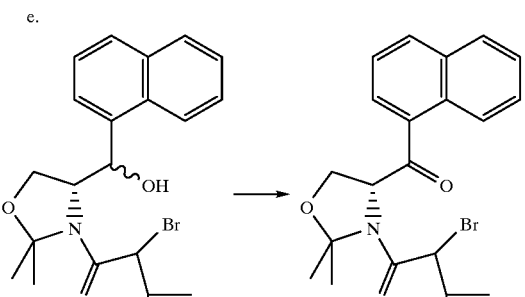

To the secondary alcohol (770 mg, 1.83 mmol), 321 mg of N-methylmorpholine-N-oxide (NMO) (2.74 mmol), and 1.80 g of 4 Å molecular sieve power in 4 mL of dichloromethane and 400 μl acetonitrile under nitrogen, was added TPAP (50 mg). The reaction mixture was stirred at room temperature for 2 hours followed by filtration through a short silica gel column. The filtrate was concentrated, and the residue was purified by flash column chromatography on silica gel with ethyl acetate-hexane (V/V=1/5) giving the ketone (560 mg, 73%) as a white foam; IR: 1693, 1643, 1415, 1233, 1073, 913, 801, 779, 731 cm−1; $^1$H NMR (CDCl$_3$) (major product) δ 7.40–8.46 (m, 7H, 7Ar-H), 5.76 (dd, 1H, J=8.4, 3.6 Hz, CHBrC(O)), 3.89–4.35 (m, 3H, OCH$_2$+NH), 2.45 (m, 1H, CHMe$_2$), 1.95 (s, 3H, Me), 1.77(s, 3H, Me), 1.24 (d, 3H, J=6.3 Hz, Me), 1.23 (d, 3H, J=6.3 Hz, Me); $^{13}$CNMR (CDCl$_3$) 198.76, 166.78, 134.52, 133.74, 132.74, 128.39, 128.08, 127.82, 126.64, 125.71, 125.22, 124.50, 94.98, 66.00, 54.60, 52.40, 33.39, 28.13, 26.64, 21.09, 19.88; MS m/z 338 (M$^+$ HBr, 11.8%), 264, 262, 155, 127, 100(100%).

f.

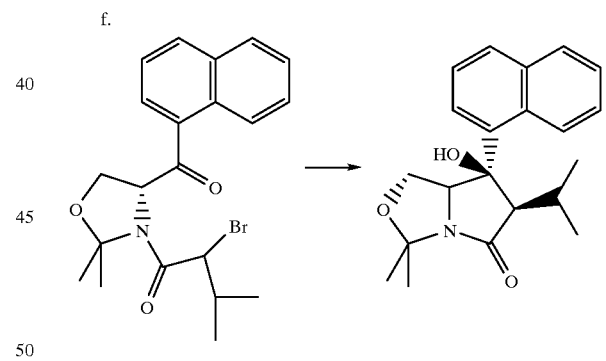

The solution of 552 mg (1.32 mmol) of the ketone and 10 mg of anhydrous FeCl$_3$ in 10 mL of THF was added slowly to 40 mL of SmI$_2$ solution (0.1M in THF) under nitrogen. After the addition, 2 mL of HMPA was added, and the mixture was stirred at room temperature for another 30 minutes followed by addition of 10 mL of ice-water. The reaction mixture was filtered through celite, and an additional 50 mL of ether was added to the filtrate. The combined organic layer was washed with water and brine (50 mL of each) and dried over MgSO$_4$. After concentration, the product was purified by flash column chromatography on silica gel with ethyl acetate-hexane (V/V=1/5) giving the tertiary alcohol (390 mg, 87%) as white crystals; [α]$_D$=+376.4° (c=1.05 in CHCl$_3$); IR: 3407, 1674, 1263, 1038, 805, 779 cm$^{-1}$; $^1$H NMR(CDCl$_3$) δ 7.40–8.15 (m, 7H, 7Ar), 4.72 (dd, 1H, J=10.2, 6.0 Hz, OCH), 3.76 (dd, 1H, J=9.0, 6.0 Hz, OC H), 3.32 (d, 1H, J=3.6 Hz, NCH), 2.47 (t, 1H, J=4.8 Hz, CHC(O)), 2.40 (m, 1H, CHMe$_2$), 2.37 (d, 1H, J=2.4 Hz, OH), 1.48 (s, 3H, Me), 1.28 (m, 9H, 3Me); $^{13}$C NMR (CDCl$_3$) δ 170.78, 137.15, 137.74, 131.61, 129.99, 129.40, 126.34, 126.21, 125.92, 124.76, 124.71, 90.83, 79.53, 60.15, 66.23, 64.06, 27.33, 26.67, 22.83×2, 19.00; MS m/z 339 (M$^+$, 0.89%), 321 (M-H2O, 0.76%), 281, 197, 169, 155 (100%), 127.69.

g.

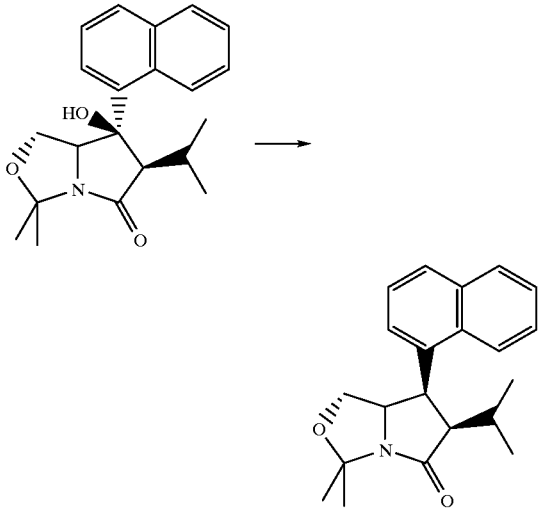

To the suspension of 63 mg of NaH (1.65 mmol, 60% in mineral oil) in 2 mL of anhydrous THF under nitrogen at 0° C., was added the solution of 100 mg of the tertiary alcohol from sub-part d below (296 μmol) in 3 mL of THF. After stirring for 30 minutes at 0° C., carbon disulfide (96 μl (1.65 μl) was added. The resulting mixture was stirred at room temperature for another hour, followed by 200 μl of methyl iodide (3.0 mmol). 2 hours later, the reaction mixture was poured into 10 ml of ice-water and extracted with 30 ml of ether. The organic layer was washed with brine and dried over MgSO$_4$. After concentration, the xanthate (68 mg, 54%) was obtained by flash chromatography on silica gel as white foam.

The solution of 68 mg of the xanthate (159 μmol), 102 μl of Bu$_3$SnH (354 μmol), and 10 mg of AIBN in 4 ml of anhydrous benzene was refluxed under nitrogen overnight. After evaporation, the residue was dissolved in 30 ml of ether, washed with aqueous KF solution and brine, adn dried over MgSO$_4$. Chromatography on silica gel (¼ ethyl aetate-hexane as eluent) provided the acetonide (35.9 mg) as a colorless oil (70%); [α]$_D$=−284.4° (c=0.23 in CHCl$_3$); IR: 1689 cm$^{-1}$; MS m/z 323 (M$^+$, 16.0%), 308 (44.0%), 196 (86.0%), 181 (100%).

EXAMPLE 4

(3R,4S,5S)-3-Isopropyl-4-(4-hexanoyloxynaphth-1-yl)-5-(hydroxymethyl)pyrrolidin-2-one (11b).

Using a procedure similar to that described in Example 6, the requisite acetonide from sub-part d below was cleaved to give the title compound; $^1$H NMR (CDCl$_3$) δ 7.92–8.01 (m, 2H), 7.60(m, 2H), 7.50(d, 1H, J=8.1 Hz), 7.23(d, 1H, J=8.1 Hz), 6.60(s,1H, OH), 4.42(br.t, 1H, J=6.3 Hz), 4.18(t, 1H, J=8.7 Hz), 3.88(br.d, 1H, J=11.1 Hz), 3.58(m, 1H), 2.94(dd, 1H, J=3.6, 9.0 Hz), 2.75(t, 2H, J=7.5 Hz), 2.52(br.s, 1H, NH), 1.87(m, 2H), 1.32–1.55(m, 5H), 0.90–0.82(m, 9H, 3Me); MS m/z 397(M$^+$,2.64%), 299(56.6%), 268, 212, 43(100%);

a.

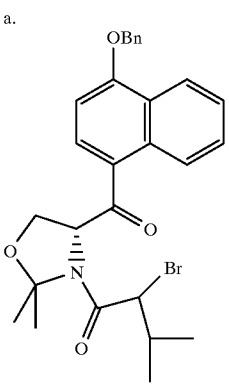

Using a procedure similar to that described in Example 3, sub-parts a–d, except replacing the naphthylmagnesium bromide used in sub-part c with the requisite 4-benzyloxynaphthylmagnesium bromide, the 4-benzyloxy intermediate was prepared; [α]$_D$=+254.8° (c=0.85 in CHCl$_3$); IR: 3413, 1674, 1264, 1089, 769, 731 cm$^{-1}$; $^1$H NMR(CDCl$_3$) δ 8.55(m, 1H), 8.46(m, 1H), 7.37–7.54(m, 8H), 6.82(d, 1H, J=8.4 Hz), 5.26(br.s, 2H, OCH$_2$Ph), 4.71 (dd, 1H, J=5.7, 9.9 Hz), 3.78(dd, 1H, J=5.7, 8.4 Hz), 3.27(d, 1H, J=3.6 Hz), 2.58(t, 1H, J=9.3 Hz), 2.46(m, 1H), 2.22(s, 1H, OH), 1.48(s, 3H, Me), 1.25–1.30(m, 9H, 3Me); $^{13}$CNMR (CDCl$_3$) δ170.92, 154.97, 136.53, 132.72, 129.21, 128.61, 128.09, 127.43, 126.79, 126.67, 126.09, 125.33, 125.08, 123.13, 103.49, 90.71, 79.24, 70.154, 66.308, 64.028, 27.22, 26.62, 22.87, 22.80, 18.99; MS m/z 445(M$^+$, 1.19), 387, 261, 91(100).

b.

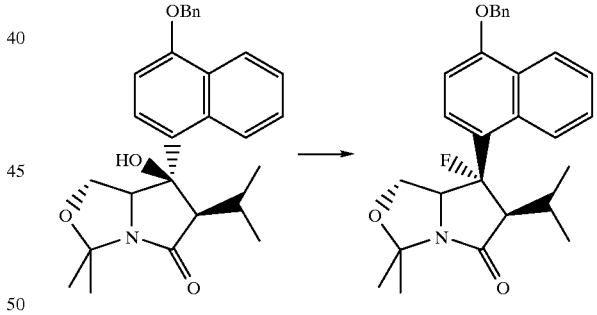

To a solution of 50 mg of the tertiary alcohol (112 μmol) in 2 mL of dichloromethane at −78° C. under nitrogen, was added DAST (44 μl, 336 μmol). The mixture was then allowed to warm to room temperature and reacted for another 2 hours. The resulting mixture was partitioned between 20 mL of dichloromethane and 10 mL of water. The organic layher was separated, washed with brine, and dried over MgSO$_4$. Evaporation and chromatography on silica gel (⅔ ethyl acetate-hexane as eluent) afforded 40.4 mg of the fluoro-compound (80%); [α]$_D$=+200.7° (c=0.54 in CHCl$_3$); IR: 1697, 1368, 1078, 1030,836, 766, 735 cm$^{-1}$; $^1$H NMR (CDCl$_3$) δ 8.45(br.d, 1H, J=7.8 Hz), 8.27(d, 1H, J=8.1 Hz), 7.31–7.61(m, 8H), 6.81(d, 1H, J=8.1 Hz), 5.28(AB.q 2H, J=12.0 Hz), 5.17(dt, 1H, J$_{H-F}$=22.5(d), 7.8(t)Hz), 4.17(m, 2H), 3.67(dd, 1H, J=20.1, 3.6 Hz), 1.77(s, 3H, Me), 1.62(s, 3H, Me), 1.42(m, 1H, CHMe$_2$), 0.88(d, 3H, J=6.9 Hz, Me), 0.78(d, 3H, J=6.9 Hz, Me); $^{13}$CNMR (CDCl$_3$) δ 170.67, 156.01, 135.43, 132.70, 128.68, 128.18, 127.56, 127.39, 125.81, 125.57, 125.49, 125.08(d, J=6.0 Hz), 123.00, 103.23, 70.24, 66.21, 65.92, 65.68, 62.14(d, J=9.3 Hz), 27.11(d, J=7.0 Hz), 26.81, 23.01, 22.13, 17.95; MS m/z 447 (M$^+$, 2.28%), 427, 320, 91(100%).

c.

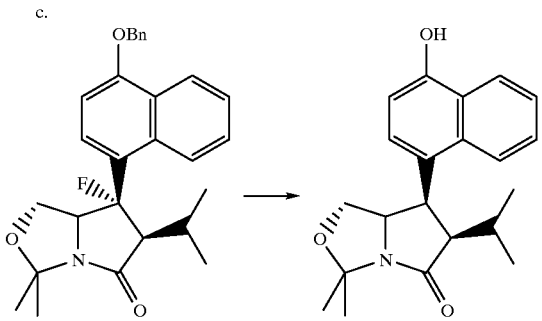

40 mg of the fluorobenzyloxy derivative (89.4 mol) and 40 mg of 5% Pd/C in 3 mL of methanol was stirred at room temperature for 14 hours under hydrogen. The resulting suspension was filtered and concentrated. Chromatography on silica gel afforded the alcohol (27.5 mg) as a white foam (90%); [α]$_D$=+245.3° (c=0.45 in CHCl$_3$); $^1$H NMR(CDCl$_3$) δ 8.30(br.d, 1H, J=7.5 Hz), 7.88(d, 1H, J=7.8 Hz), 7.50–7.60 (m, 2H), 7.31(d, 1H, J=7.8 Hz), 6.82(d, 1H, J=7.8 Hz), 6.16(s, 1H, OH), 4.96(ddd, 1H, J=5.4, 9.3, 14.7 Hz), 4.22 (dd, 1H, J=8.7,6.7 Hz), 4.10(m, 1H), 3.55(t, 1H, J=8.7 Hz), 3.24(dd, 1H, J=3.6, 8.7 Hz), 1.80(s, 3H, Me), 1.61(s, 3H, Me), 1.40(m, 1H, CHMe$_2$), 0.86(d, 3H, J=6.9 Hz, Me), 0.79(d, 3H, J=6.9 Hz, Me); $^{13}$C NMR (CDCl$_3$) δ 171.82, 151.50, 133.16, 127.18, 125.34, 125.00, 124.28, 123.59, 122.92, 122.78, 107.52, 91.53, 69.76, 62.61, 59.32, 45.83, 27.04, 26.83, 23.81, 22.30, 18.67; MS m/z 339 (M$^+$, 24.7%), 212(100%), 197(51.1%)

d.

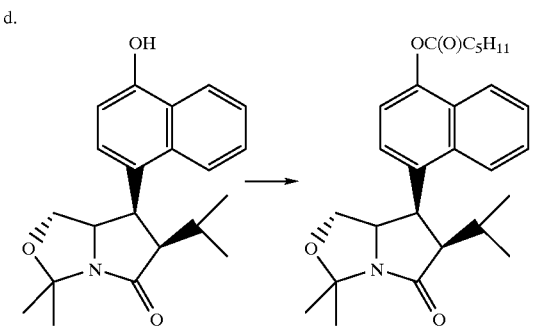

To the solution of 4.0 mg of the naphthol compound (11.8 μmol) in 200 μl of anmhydrous pyridine under nitrogen, was added hexanoyl chloride (10.6 μl, 60 μmol). The reaction mixture was allowed to stir at room temperature overnight. The resulting solution was diluted with 30 mL of ether, washed with 5 mL of 1N HCl and brine, and dried over MgSO$_4$. Concentration and purification by TLC afforded the ester (4.8 mg, 93%); $^1$H NMR(CDCl$_3$) δ 7.95(m, 2H), 7.57(m, 2H), 7.48(d, 1H, J=7.8 Hz), 7.23(d, 1H, J=7.8 Hz), 4.99(ddd, 1H, J=5.7, 9.0, 14.7 Hz), 4.22(dd, 1H, J=5.7, 8.7 Hz0, 4.14(t, 1H, J=9.0 Hz), 3.54(t, 1H, J=8.4 Hz), 3.24(dd, 1H, J=3.6, 8.7 Hz), 2.75(t, 2H, J=7.5 Hz), 1.87(t, 2H, J=7.5 Hz), 1.79(s, 3H, Me), 1.60(s, 3H, Me),135–1.55(m, 5H), 0.96(t, 3H, J=6.9 Hz, Me), 0.87(d, 3H, J=6.9 Hz, Me), 0.79(d, 3H, J=6.9 Hz, Me); $^{13}$CNMR (CDCl$_3$) δ 172.27, 171.23, 146.29, 133.13, 130.41, 127.22, 126.57, 123.34, 122.14, 117.27, 91.55, 69.70, 62.45, 59.37, 46.05, 34.38, 31.36, 27.06, 26.83, 24.74, 23.77, 22.36, 18.64, 13.95; MS m/z 437(M$^+$, 3.1%), 339, 212(100%), 197,43.

EXAMPLE 5

(3R,4S,5S)-3-Isopropyl-4-(4-nonanoyloxynaphth-1-yl)-5-(hydroxymethyl)pyrrolidin-2-one (11c)

Using a procedure similar to that described in Example 6, the requisite acetonide (prepared below was cleaved to give the title compound; $^1$HNMR(CDCl$_3$) δ7.92–8.01(m, 2H), 7.60(m, 2H), 7.50(d, 1H, J=8.1 Hz), 7.23(d, (3R,4S,5S)-3-Isopropyl-4-(4-J=8.1 Hz), 6.65(s,1H, OH), 4.42(br.t, 1H, J=6.3 Hz), 4.18(t, 1H, J=8.7 Hz), 3.88(br.d, 1H, J=11.1 Hz), 3.58(m, 1H), 2.94(dd, 1H, J=3.6, 9.0 Hz), 2.75(t, 2H, J=7.5 Hz), 2.58(br.s, 1H, NH), 1.87(m, 2H), 1.30–1.55(m, 11H), 0.90–0.82(m, 9H, 3Me); MS m/z 439(M$^+$, 4.75%, 299 (100%), 268, 212, 57, 43.

The intermediate acetonide was prepared as follows.

Using a procedure similar to tha described in Example 4 sub-part d, except replacing the hexanoyl chloride used therein with nonanoyl chloride, the title compound was prepared; $^1$H NMR(CDCl$_3$) δ 7.95(m, 2H), 7.57(m, 2H), 7.48(d, 1H, J=7.8 Hz), 7.23(d, 1H, J=7.8 Hz), 4.99(ddd, 1H, J=5.7, 9.0, 14.7 Hz), 4.22(dd, 1H, J=5.7, 8.7 Hz), 4.14(t,1H, J=9.0 Hz), 3.54(t, 1H, J=8.4 Hz), 3.24(dd, 1H, J=3.6, 8.7 Hz), 2.75(t, 2H, J=7.5 Hz), 1.87(t, 2H, J=7.5 Hz), 1.79(s,3H, Me), 1.60(s, 3H, Me),1.45–1.55(m, 11H), 0.88(br.t, 6H, J=6.9 Hz, 2Me) 0.79(d, 3H, J=6.9 Hz, Me); $^{13}$CNMR (CDCl$_3$) δ 172.28, 171.26, 146.29, 133.14, 130.41, 127.22, 126.57, 123.34, 122.16, 117.28, 91.56, 69.71, 62.47, 59.37, 46.05, 34.43, 31.81, 29.25, 29.22, 29.15, 27.07, 26.83, 25.61, 23.77, 22.66, 22.29, 18.64, 14.11; MS m/z 479(M$^+$, 1.98%), 339, 212(100%), 197, 57, 43.

EXAMPLE 6

(3R,4S,5S)-3-Isopropyl-4-[4-(heptyn-1-yl)naphth-1-yl]-5-(hydroxymethyl)pyrrolidin-2-one (11d)

To the solution of 3.0 mg of the heptyne-derivative from sub-part b below (7.2 μmol) and 10 μl of 1,2-ethanedithiol in 400 μl of anhydrous dichloromethane at room temperature under nitrogen, was added 4 μl of BF$_3$·Et$_2$O (14.5 μmol). After 7 minutes, 1 mL of aqueous sat. NaHCO$_3$ was added, and the mixture was extracted with 20 mL of ethyl acetate. After concentration, the residue was purified by TLC to give 2.16 mg of the title compound (80%); $^1$H NMR (CDCl$_3$) δ 8.44(m, 1h), 7.98(m, 1H), 7.60(m, 3H), 7.44(d, 2H, J=7.8 Hz) 6.50(s,1H, OH), 4.42(br.t, 1H, J=5.7 Hz), 4.19(t, 1H, J=9.0 Hz), 3.87(br.d, 1H, J=10.8 Hz), 3.59(m, 1H), 2.94(dd, 1H, J=3.6, 9.0 Hz), 2.57(t, 2H, J=6.9 Hz), 2.31(br.s, 1H, NH), 1.72(m, 2H), 1.30–1.60(m, 5H), 0.96(t, 3H, J=6.9, Me), 0.85(d, 3H, J=6.9 Hz, Me), 0.82(d, 3H, J=6.9 Hz, Me); MS m/z 377(M$^+$, 100%), 346, 304, 209, 43;

The intermediate heptyne derivative was prepared as follows.

a.

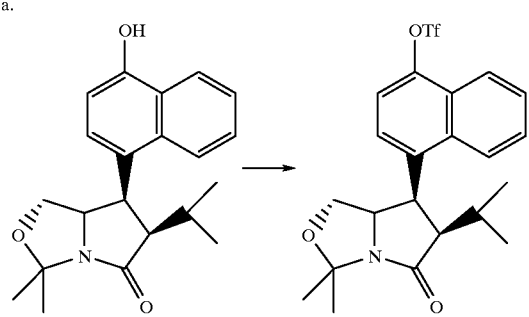

To the stirring solution of 14.0 mg of the naphthol derivative (41.3 μmol) and 100 μl of 2,6-lutidine in 200 μl of anhyudrous dichloromethane at −78° C. under nitrogen, was added 220 μl of trifluoromethanesulfonic anhydride solution (166 μmol, 0.74M in dichloromethane). After 30 minutes at −78° C., the reaction mixture was poured into 5 mL of 1N HCl and extracted with 30 mL of ether. The organic layer was washed with brine and dried over MgSO$_4$. Concentration and purification by TLC gave the corresponding triflate (13.6 mg, 70%); $^1$H NMR(CDCl$_3$) δ 8.14(m, 1), 8.01(m, 1H), 7.71(m, 2H), 7.46(q, 2H, J=8.1 Hz), 4.99(ddd, 1H, J=5.7, 9.3, 14.7 Hz), 4.22(dd, 1H, J=5.4, 8.4 Hz), 4.16(t,1H, J=9.0 Hz), 3.55(t, 1H, J=8.4 Hz), 3.24(dd, 1H, J=3.6, 8.4 Hz), 1.79(s,3H, Me), 1.61(s, 3H, Me),1.26(m, 1H), 0.86(d, 3H, J=6.9 Hz, Me), 0.79(d, 3H, J=6.9 Hz, Me); MS m/z 471(M$^+$), 456, 344, 211(100%.

b.

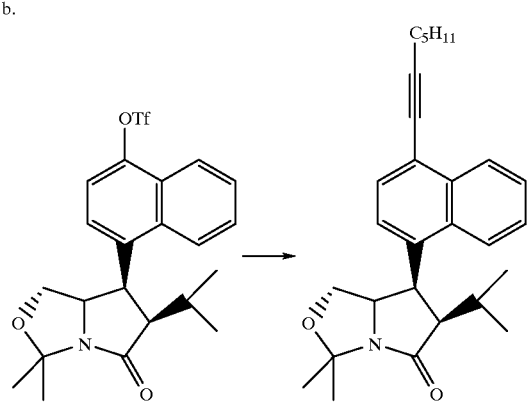

To the mixture of 5.6 mg of the triflate, 1 mg of PdCl$_2$(PPh$_3$)$_2$ 100 μl of Et$_3$N, and 100 μl of DMF under argon, was added 20 μl of the 1-heptyne and 0.5 mg of CuI. The resulting solution was stirred overnight at 50° C., then partitioned between 20 mL of ether and 5 mL of water. After concentration, the product was purified on TLC giving the heptynyl derivative (3.0 mg, 61%) as colorless oil; $^1$H NMR(CDCl$_3$) δ 8.42(m, 1H), 7.93(m, 1H), 7.60(m, 3H), 7.42(d, 2H, J=7.5 Hz) 5.00(ddd, 1H, J=5.7, 9.0, 14.7 Hz), 4.22(dd, 1H, J=5.7, 8.7 Hz), 4.16(t,1H, J=9.3 Hz), 3.54(t, 1H, J=8.4 Hz), 3.24(dd, 1H, J=3.6, 8.7 Hz), 2.57(t, 2H, J=7.2 Hz), 1.78(s, 3H, Me), 1.70(t, 2H, J=7.5 Hz), 1.60(s, 3H, Me), 1.30–1.55(m, 5H), 0.96(t, 3H, J=6.9, Me), 0.84(d, 3H, J=6.9 Hz, Me), 0.77(d, 3H, J=6.9 Hz, Me); $^{13}$C NMR(CDCl$_3$) δ171.22, 133.70, 132.43, 131.86, 129.24, 127.50, 127.00, 126.60, 123.19, 123.07, 121.92, 96.33, 91.55, 78.22, 69.68, 62.32, 59.49, 46.18, 31.22, 28.57, 27.09, 26.85, 23.78, 22.26, 29.72, 28.61, 14.04; MS m/z 417(M$^+$, 35.5%), 290 (100%, 84, 43.

EXAMPLE 7

(3R,4S,5S)-3-Isopropyl-4-(7,7-dimethyl-4-nonanoyloxy-5,6,7,8-tetrahydronaphth-1-yl)-5-(hydroxymethyl)pyrrolidin-2-one (15a)

Compound 14a was treated with tetrabutylammonium fluoride under standard conditions to remove the TBS protecting group and give the corresponding primary alcohol., Hydrogenation under conditions similar to those described in Example 1, sub-part e gave the correspojnding isopropyl compound, which was treated with trifluoroacetic acid under standard conditions to give compound 15a; $^1$H NMR (CDCl$_3$): δ 7.19(d, 1H, J=8.4 Hz), 6.90(d, 1H, J=8.4 Hz), 6.24(br s, 1H), 3.69, 3.59(br AB q, 2H, J=10.8), 3.43(br t, 2H, J=8.7 Hz), 2.75(dd, 1H, J=3.6, 10.2 Hz), 2.63–2.50(m, 6H), 2.18(m, 1H), 2.05(br s, 1H), 1.77(m, 2H), 1.60(br s, 1H), 1.52(t, 2H, J=6.9 Hz), 1.43–1.25(m, 10H), 0.99(s, 9H), 0.89(t, 3H, J=6.9 Hz), 0.76(d, 3H, J=7.2 Hz); MS m/z 471(M$^+$).

Figure 3:
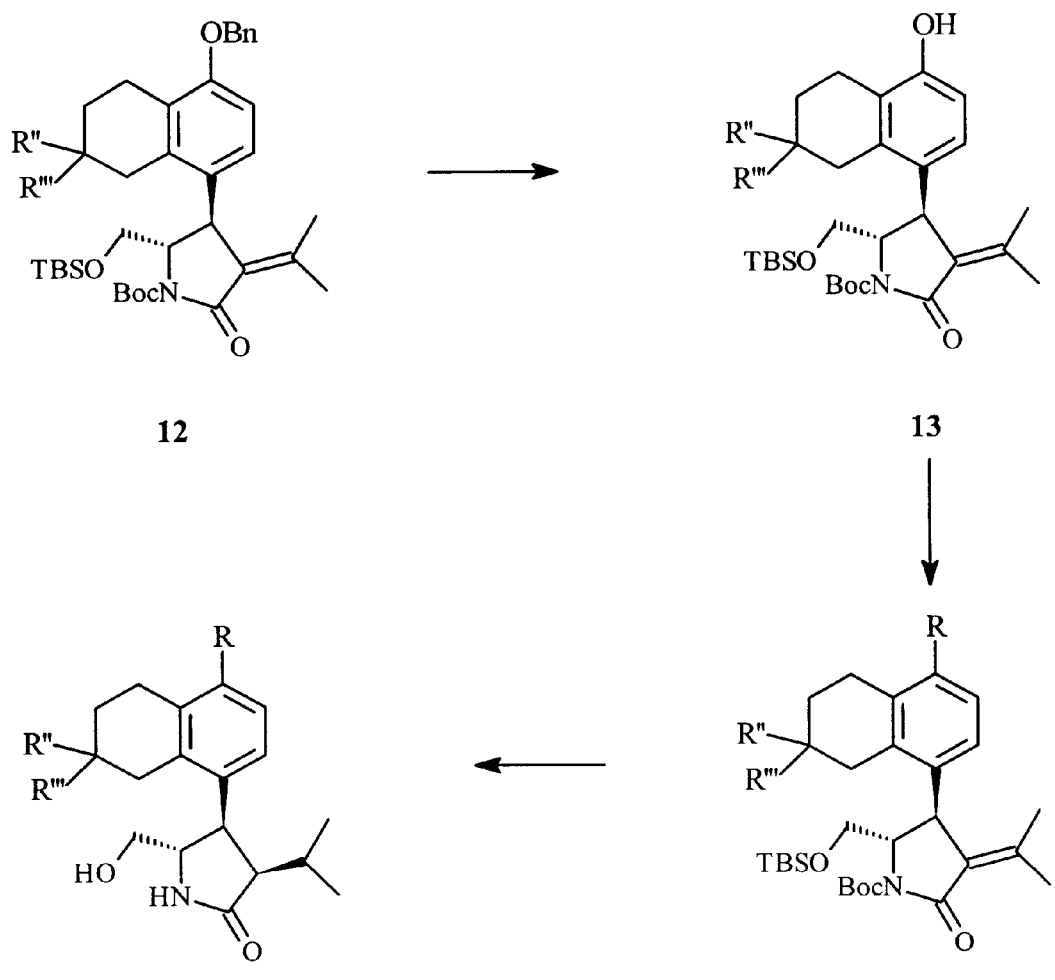

The intermediate compound 14a was prepared as follows.

a. Compound 12 (FIG. 3, wherein R" and R'" are each methyl) was prepared using methods similar to those described in Example 1 sub-parts a–c, by replacing the 4-bromophenyl Grignard reagent used in sub-part a with the requisite Grignard reagent.

b. Compound 12 (260 mg) was hydrogenated over 40 mg of 10% Pd/C in 8 mL of methanol until it could no longer to detected using TLC (ca. 2 hours). The reaction mixture was filtered through Celite and concentrated to give compound 13 (FIG. 3, whrein R' and R'" are each methyl).

c. The alcohol from sub-part b (50 mg) was acylated with 50 μl of nonanoyl chloride in 200 μl of pyridine. Purification with column chnromatography, gave compound 14a as a colorless oil (93%); [α]$_D$=−72.7° (c=1.33 in CHCl$_3$); IR (film): 1759, 1731, 1709, 1659 cm$^{-1}$; $^1$H NMR (CDCl$_3$): d 6.87(d, 1H, J=7.8 Hz), 6.75(d, 1H, J=7.8 Hz), 4.13(br s, 1H), 3.82(m, 2H), 3.75(t, 1H, J=3.0 Hz), 2.63–2.46(m, 6H), 2.31(s, 3H), 1.76(m, 2H), 1.57(s, 3H), 1.54(m, 2H), 1.51(s, 9H), 1.43–1.25(m, 10H), 1.02, 1.00(two s, 3H each), 0.88(br s, 12H), 0.68, 0.15 (two s, 3H each).

EXAMPLE 8

(3R,4S,5S)-3-Isopropyl-4-(4-nonanoyloxy-5,6,7,8-tetrahydronaphth-1-yl)-5-(hydroxymethyl)pyrrolidin-2-one (15b)

Using procedures similar to thsoe described in Example 7, compound 14a was converted to compound 15b; $^1$H NMR (CDCl$_3$): δ 7.17(d, 1H, J=8.4 Hz), 6.88(d, 1H, J=8.4 Hz), 6.08(br s, 1H), 3.73(br d, 1H, J=11.1 Hz), 3.61(m, 1H), 3.45(m, 2H), 2.76(m, 3H), 2.56(m, 4H), 21.18(m, 1H), 1.96–1.68(m, 7H), 1.50–1.26(m, 10H), 1.00(d, 3H, J=6.9 Hz), 0.89(t, 1H, J=6.9 Hz), 0.79(d, 1H, J=6.9 Hz); MS m/z 443(M$^+$), 303(M$^+$-nonanoyl).

The intermediate compound 14b was prepared as follows.

a. Compound 12 (FIG. 3, wherein R' and R'" are each hydrogen) was prepared using methods similar to those descried in Example 1 sub-parts a–c, by replacing the 4-bromophenyl Grignard reagent used ins ub-part a with the requisite Grignard reagent.

b. Compound 12 (FIG. 3, wherein R' and R'" are each hydrogen; 260 mg) was hydrogenated over 40 mg of 10% Pd/C in 8 mL of methanol until it could no longer be detected using TLC (ca. 2 hours). The reaction mixture was filtered through Celite and concentrated to give compound 13 (FIG. 3, wherein R' and R'" are each methyl).

c. The alcohol from sub-part b (50 mg) was acylated with 50 µL of nonanoyl chloride in 200 µL of pyridine to give compound 14b.

EXAMPLE 9

(3R,4S,5S)-3-Isopropyl-4-(4-hexanoyloxy-5,6,7,8-tetrahydronaphth-1-yl)-5-(hydroxymethyl) purrolidin-2-one (15c)

Using procedures similar to those described in Example 7, compound 14c was converted to compound 15c; $^1$H NMR (CDCl$_3$): δ 7.17(d, 1H, J=8.4 Hz), 6.889d, 1H, J=8.4 Hz), 6.09(br s, 1H), 3.73(br d, 1H, J=11.1 Hz), 3.61(dt, 1H, J=3.3 Hz (d), 6.9(t)), 3.45(br t, 2H, J=7.5 Hz), 2.76(m, 3H), 2.58(m, 4H), 2.18(m, 1H), 1.96–1.68(m, 7H), 1.50–1.32(m, 4H), 1.00(d, 3H, J=6.9 Hz), 0.95(t, 1H, J=7.2 Hz), 0.80(d, 1H, J=6.9 Hz); MS m/z 401(M$^+$), 303 (M$^+$-hexanoyl).

The intermediate compound 14c was prepared by acylation of the compound prepared in Example 8, sub-part b with hexanoyl chloride, under conditions similar to those described in Example 8, sub-part c.

EXAMPLE 10

(3R,4S,5S)-3-Isopropyl-4-(7-spirocyclopropyl-4-nonanoyloxy-5,6,7,8-tetrahydronaphth-1-yl)-5-(hydroxymethyl)pyrrolidin-2-one (15d)

Using procedures similar to those described in Example 7, compound 14d was converted to compound 15d; $^1$H NMR (CDCl$_3$): δ 7.18(d, 1H, J=8.4 Hz), .691(d, 1H, J=8.4 Hz), 6.09(br s, 1H), 3.67(br d, 1H, J=11.7 Hz), 3.58(m, 1H), 3.43–3.28(m, 2H), 2.76–2.62(m, 4H), 2.56(m, 3H), 2.16(m, 1H), 1.88(br s, 1H), 1.75(m, 2H), 1.60–1.24(m, 10H), 0.96 (d, 3H, J=6.6 Hz), 0.88(t, 1H, J=6.6 Hz), 0.75(d, 1H, J=6.9 Hz), 0.42(d, 4H, J=9.3 Hz); MS m/z 469 (M$^+$), 329(M$^+$-nonanoyl).

The intermediate compound 14d was prepared as follows.

a. Compound 12 (FIG. 3, wherein R' and R''' together with the carbon to which they are attached form a spirocyclopropane) was prepared using methods similar to those descried in Example 1 sub-parts a–c, by replacing the 4-bromophenyl Grignard reagent used in sub-part a with the requisite Grignard reagent.

b. Compound 12 (FIG. 3, wherein R'' and R''' together with the carbon to which they are attached form a spirocyclopropane; 260 mg) was hydrogenated over 40 mg of 10% Pd/C in 8 mL of methanol until it could no longer be detected using TLC. The reaction mixture was filtered through Celite and concentrated to give compound 13 (FIG. 3, wherein R'' and R''' together with the carbon to which they are attached form a spirocyclopropane).

c. The alcohol from sub-part b (50 mg) was acylated with 50 mL of nonanoyl chloride in 200 mL of pyridine. Purification with column chromatography, gave compound 14d as a colorless oil.

EXAMPLE 11

(3R,4S,5S)-3-(2-Ethylbut-1-yl)-4-(3-pentyl)-5-(hydroxymethyl)-pyrrolidin-2-one (15d)

Using a synthetic sequence similar to that described in Example 1 and the sub-parts thereof, except replacing the 4-bromophenyl Grignard reqgent usedin sub-part a with the requisite 3-pentyl Grignard reagent, and replacing the acetone usedin sub-part b with the requisite 2-ethylbutyraldehyde, the title copound was prepared; [α]$_D$=+37.7° (c=0.57 in CHCl$_3$); $^1$H NMR (CDCl$_3$): δ 7.01(s, 1H), 3.80(br s, 1H), 3.63(d, 1H, J=8.1 Hz), 3.40(m, 2H), 2.22(m, 1H), J=3.3, 4.5 Hz), 1.65 (m, 1H), 1.48–1.10 (m, 11H), 0.95–0.83(m, 12H).

All publications, patents, and patent documents are incorporated by referene herein, as though individually incorporated by reference. The invention has been described with reference to various specific and preferred embodiments and techniques. However, it should be understood that many vatiations and modifications may be made while remaining within the spirit and scope of the invention.

What is claimed is:

1. A compound of formula I:

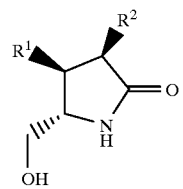

(I)

wherein

R$^1$ and R$^2$ are each independently (C$_1$–C$_{15}$)alkyl, (C$_2$–C$_{15}$)alkenyl, (C$_2$–C$_{15}$)alkynyl, (C$_3$–C$_8$)cycloalkyl, (C$_3$–C$_8$)cycloalkyl(C$_1$–C$_{10}$)alkyl, (C$_3$–C$_8$)cycloalkyl (C$_1$–C$_{15}$)alkenyl, C$_3$–C$_8$)cycloalkyl(C$_1$–C$_{15}$)alkynyl, (C$_1$–C$_{15}$)alkoxy, (C$_1$–C$_{15}$)alkanoyl, (C$_1$–C$_{15}$) alkanoyloxy, aryl heteroaryl, aryl(C$_1$–C$_6$)alkyl, heteroaryl(C$_1$–C$_6$)alkyl, aryl(C$_2$–C$_{15}$)alkenyl, heteroaryl(C$_2$–C$_{15}$)alkenyl, aryl(C$_2$–C$_{15}$)alkynyl, heteroaryl(C$_2$–C$_{15}$)alkynyl, aryl(C$_1$–c$_{15}$)alkoxy, heteroaryl(C$_1$–C$_{15}$)alkoxy, aryl(C$_1$–C$_{15}$)alkanoyl, heteroaryl(C$_1$–C$_{15}$)alkanoyl, aryl(C$_1$–C$_{15}$)alkanoyloxy, or heteroaryl(C$_1$–C$_{15}$)alkanoyloxy;

wherein R$^1$ and R$^2$ is optionally substituted with one ore more substituents independently selected from the group consisting of halo, nitro, cyano, hydroxy, trifluoromethyl, trifluoromethoxy, (C$_1$–C$_{15}$)alkyl, )C$_2$–C$_{15}$)alkenyl, (C$_2$–C$_{15}$)alkynyl (C$_3$–C$_8$)cycloalkyl, (C$_3$–C$_8$)cycloalkyl(C$_1$–C$_{15}$)alkyl, (C$_3$–C$_8$)cycloalkyl-(C$_2$–C$_{15}$)alkenyl, (C$_3$–C$_8$)cycloalkyl(C$_2$–C$_{15}$)alkynyl, (C$_1$–C$_{15}$)alkoxy, (C$_1$–C$_{15}$)alkanoyl, (C$_1$–C$_{15}$) alkanoyloxy, C(=O)OR$_a$, C(=O)NR$_b$R$_c$, OC(=O) OR$_a$, OC(=O)NR$_b$R$_c$, and NR$_e$R$_f$; and wherein any aryl or heteroaryl or R$^1$ or R$^2$ is optionally substituted on a non-aromatic carbon by a divalent (C$_2$–C$_7$) alkylene chain to form a (C$_3$–C$_8$)spirocycloalkyl;

each R$_a$ is independently hydrogen or (C$_1$–C$_6$)alkyl;

each R$_b$ and R$_c$ is independently, hydrogen or (C$_1$–C$_{10}$) alkyl; or R$_b$, and R$_c$ together with the nitrogen to which they are attached are a 5–6 membered heterocyclic ring; and each R$_e$ and R$_f$ is independently hydrogen, (C$_1$–C$_{10}$)alkyl, (C$_1$–C$_{10}$)alkanoyl, phenyl, benzyl, or phenethyl; or R$_e$ and R$_f$ together with the nitrogen to which they are attached are a 5–6 membered heterocyclic ring;

or a pharmaceutically acceptable salt thereof.

2. The compound of claim 1 wherein R$^1$ is (C$_1$–C$_{15}$)alkyl, (C$_2$–C$_{15}$)alkenyl, (C$_2$–C$_{15}$)alkynyl, (C$_3$–C$_8$)cycloalkyl, (C$_3$–C$_8$)cycloalkyl(C$_1$–C$_{10}$)alkyl, (C$_3$–C$_8$)cycloalkyl (C$_1$–C$_{15}$)alkenyl, C$_3$–C$_8$)cycloalkyl(C$_1$–C$_{15}$)alkynyl, (C$_1$–C$_{15}$)alkoxy, (C$_1$–C$_{15}$)alkanoyl, (C$_1$–C$_{15}$)alkanoyloxy;

wherein $R^1$ is optionally substituted with one or more substituents independently selected from the group consisting of halo, nitro, cyano, hydroxy, trifluoromethyl, trifluoromethoxy, $C(=O)NR_bR_c$, $OC(=O)OR_a$, $OC(=O)NR_bR_c$, and $NR_eR_f$.

3. The compound of claim 1 wherein $R^1$ is aryl, heteroaryl, aryl($C_1$–$C_6$)alkyl, heteroaryl($C_1$–$C_6$)alkyl, aryl ($C_2$–$C_6$)alkenyl, heteroaryl($C_2$–$C_6$)alkenyl, aryl($C_2$–$C_6$) alkynyl, or heteroaryl($C_2$–$C_6$)alkynyl; wherein any aryl or heteroaryl of $R^1$ is optionally substituted with one or more substituents independently selected from the group consisting of halo, nitro, cyano, hydroxy, trifluoromethyl, trifluoromethoxy, ($C_1$–$C_{15}$)alkyl, ($C_2$–$C_{15}$)alkenyl, ($C_2$–$C_{15}$)alkynyl, ($C_3$–$C_8$)cycloalkyl, ($C_3$–$C_8$)cycloalkyl ($C_1$–$C_{10}$)alkyl, ($C_3$–$C_8$)cycloalkyl($C_1$–$C_{15}$)alkenyl, $C_3$–$C_8$ cycloalkyl($C_1$–$C_{15}$)alkynyl, ($C_1$–$C_{15}$)alkoxy, ($C_1$–$C_{15}$) alkanoyl, ($C_1$–$C_{15}$)alkanoyloxy, $C(=O)OR_a$, $C(=O)$ $NR_bR_c$, $OC(=O)OR_a$, $OC(=O)NR_bR_c$, and $NR_eR_f$; and wherein any aryl or heteroaryl of $R^1$ is optionally substituted on a non-aromatic carbon by a divalent ($C_2$–$C_7$)alkylene chain to form a ($C_3$–$C_8$)spirocycloalkyl.

4. The compound of claim 1 wherein $R^1$ is phenyl or hnaphthyl, wherein said phenyl or naphthyl is optionally substituted with one or more substituents independently selected from the group consisting of halo, nitro, cyano, hydroxy, trifluoromethyl, trifluoromethoxy, ($C_1$–$C_6$)alkyl, ($C_2$–$C_6$)alkenyl, ($C_2$–$C_6$)alkynyl, ($C_3$–$C_8$)cycloalkyl, ($C_3$–$C_8$)cycloalkyl($C_1$–$C_6$)alkyl, )$C_3$–$C_8$)cycloalkyl($C_2$–$C_6$) alkenyl, ($C_3$–$C_8$)cyucloalkyl($C_2$–$C_6$alkynyl, ($C_1$–$C_6$)alkoxy, ($C_1$–$C_6$)alkanoyl, ($C_3$–$C_6$)alkanoyloxy, $C(=O)OR_a$, $C(=O)NR_bR_c$, $OC(=O)OR_a$, $OC(=O)NR_bR_c$, and $NR_eR_f$.

5. The compound of claim 1 wherein $R^1$ is phenyl or naphthyl, wherein said phenyl or naphthyl is substituted with ($C_1$–$C_{15}$)alkyl, ($C_2$–$C_{15}$)alkenyl, ($C_2$–$C_{15}$0alkynyl, ($C_1$–$C_{15}$)alkoxy, ($C_1$–$C_{15}$)alkanoyl, or ($C_1$–$C_{15}$) alkanoyloxy, and can also be optionallly substituted with 1 or 2 halo, nitro, cyano, hydroxy, trifluoromethyl, trifluoromethoxy, ($C_1$–$C_6$)alkyl, ($C_3$–$C_8$)cycloalkyl, ($C_1$–$C_6$)alkoxy, ($C_1$–$C_6$alkanoyl, ($C_2$–$C_6$)alkanoyloxy, $C(=O)OR_a$, $C(=O)NR_bR_c$, or $NR_eR_f$.

6. The compound of claim 1 wherein $R^1$ is phenyl substituted with ($C_7$–$C_{10}$)alkyl, ($C_7$–$C_{10}$)alkenyl, ($C_7$–$C_{10}$) alkynyl, ($C_7$–$C_{10}$)alkoxy, ($C_7$–$C_{10}$)alkanoyl, or ($C_7$–$C_{10}$) alkanoyloxy.

7. The compound of claim 6 wherein the phenyl is substituted at the 4 position.

8. The compound of claim 1 wherein $R^1$ is naphthyl, optionally substituted with one or more ($C_1$–$C_{15}$)alkyl, ($C_2$–$C_{15}$)alkenyl, ($C_2$–$C_{15}$)alkynyl, ($C_1$–$C_{15}$)alkoxy, ($C_1$–$C_{15}$)alkanoyl, or ($C_1$–$C_{15}$)alkanoyloxy.

9. The compound of claim 1 wherein $R^1$ is 5,6,7,8-tetrahydronaphthyl, optionally substituted with one or more ($C_1$–$C_{15}$)alkyl, ($C_2$–$C_{15}$)alkenyl, ($C_2$–$c_{15}$)alkynyl, ($C_1$–$C_{15}$) alkoxy, ($C_1$–$C_{15}$)alkanoyl, or ($C_1$–$C_{15}$)alkanoyloxy, and optionally substituted at the 5,6,7, or 8 position with a divalent ($C_2$–$C_7$)alkylene chain to form a ($C_3$–$C_8$) spirocycloalkyl.

10. The compound of claim 1 wherein $R^2$ is ($C_1$–$C_{15}$) alkyl, ($C_2$–$C_{15}$)alkenyl, ($C_2$–$C_{15}$)alkynyl, ($C_1$–$C_{15}$)alkoxy, ($C_1$–$C_{15}$)alkanoyl, or ($C_1$–$C_{15}$)alkanoyloxy; wherein said $R^2$ is optionally substituted with one ore more substituents independently selected from the group consisting og halo, nitro, cyano, hydroxy, trifluoromethyl, trifluoromethoxy, ($C_1$–$C_6$)alkoxy, ($C_1$–$C_6$)alkanoyl, ($C_1$–$C_6$)alkanoyl, ($C_2$–$C_6$)alkanoyloxy, $C(=O)OR_a$, $C(=O)NR_bR_c$, and $NR_eR_f$.

11. The compound of claim 1 wherein $R^2$ is ($C_1$–$c_{15}$)alkyl, ($C_2$–$C_{15}$)alkenyl, or ($C_2$–$C_{15}$)alkynyl.

12. The compound of claim 1 wherein $R^2$ is isopropyl.

13. The compound of claim 1 wherein $R^1$ is aryl, heteroaryl, aryl($C_1$–$C_6$)alkyl, heteroaryl($C_1$–$C_6$)alkyl, aryl ($C_2$–$C_6$)alkenyl, or heteroaryl($C_2$–$C_6$)alkenyl;

$R^2$ is ($C_1$–$C_{10}$)alkyl, ($C_2$–$C_{10}$)alkenyl, ($C_3$–$C_8$)cycloalkyl, ($C_3$–$C_8$)cycloalkyl($C_1$–$C_6$alkyl, ($C_1$–$C_{10}$)alkoxy, ($C_1$–$C_{10}$)alkanoyl, ($C_1$–$C_{10}$)alkanoyloxy, aryl, heteroaryl, aryl($C_1$–$C_6$)alkyl, or heteroaryl ($C_1$–$C_6$alkyl;

wherein any $R^1$ and $R^2$ is optionally substituted with 1, 2, or 3 substituents independently selected from the group consisting of halo, nitro, cyano, hydroxy, trifluoromethyl, trifluoromethoxy, ($C_1$–$C_6$)alkyl, ($C_2$–$C_{10}$)alkenyl, ($C_2$–$C_{10}$)alkynyl, ($C_3$–$C_8$)cycloalkyl, ($C_3$–$C_8$)cycloalkyl($C_1$–$C_6$)alkyl, ($C_1$–$C_{10}$)alkoxy, ($C_1$–$C_{10}$)alkanoyl, ($C_2$–$C_{10}$)alkanoyloxy, $C(=O)OR_a$, $C(=O)NR_bR_c$, or $NR_eR_f$;

$R_a$ is hydrogen or ($C_1$–$C_6$)alkyl;

$R_b$, and $R_c$ are each independently hydrogen or ($C_1$–$C_{10}$) alkyl; or $R_b$, and $R_c$ together with the nitrogen to which they are attached are a 5–6 membered heterocyclic ring; and $R_e$ and $R_f$ are each independently hydrogen, ($C_1$–$C_{10}$) alkyl, ($C_1$–$C_{10}$)alkanoyl, phenyl, benzyl, or phenethyl; or $R_e$ and $R_f$ together with the nitrogen to which they are attached are a 5–6 membered heterocyclic ring;

or a pharmaceutically acceptable salt thereof.

14. The compound of claim 1 wherein $R^1$ is aryl wherein said aryl is optionally substituted with one or more substituents independently selected from the group consisting of halo, nitro, cyano, hydroxy, trifluoromethyl, trifluoromethoxy, ($C_1$–$C_{15}$)alkyl, )$C_2$–$C_{15}$)alkenyl, ($C_2$–$C_{15}$)alkynyl ($C_3$–$C_8$)cycloalkyl, ($C_3$–$C_8$)cycloalkyl ($C_1$–$C_{15}$)alkyl, ($C_3$–$C_8$)cycloalkyl-($C_2$–$C_{15}$)alkenyl, ($C_3$–$C_8$)cycloalkyl($C_2$–$C_{15}$)alkynyl, ($C_1$–$C_{15}$)alkoxy, ($C_1$–$C_{15}$)alkanoyl, ($C_1$–$C_{15}$)alkanoyloxy, $C(=O)OR_a$, $C(=O)NR_bR_c$, $OC(=O)OR_a$, $OC(=O)NR_bR_c$, and $NR_eR_f$; and $R^2$ is ($C_1$–$C_{15}$)alkyl, ($C_2$–$C_{15}$)alkenyl, ($C_2$–$C_{15}$)alkynyl, ($C_1$–$C_{15}$)alkoxy, or ($C_1$–$C_{15}$)alkanoyloxy; wherein said $R^2$ is optionally substituted with one ore more substituents independently selected from the group consisting of halo, nitro, cyano, hydroxy, trifluoromethyl, trifluoromethoxy, ($C_1$–$C_6$)alkoxy, ($C_1$–$C_6$)alkanoyl, ($C_2$–$C_6$)alkanoyloxy, $C(=O)OR_a$, $C(=O)NR_bR_c$, and $NR_eR_f$;

or a pharmaceutically acceptable salt thereof.

15. The compound (3R,4S,5S)-3-isoproppyl-4-(4-nonanoyloxynaphth-1-yl)-5-(hydroxymethyl)pyrrolidin-2-one; or a pharmaceutically acceptable salt thereof.

16. A pharmaceutical composition comprising a compound of claim 1 in combination with a pharmaceutically acceptable carrier.

* * * * *

UNITED STATES PATENT AND TRADEMARK OFFICE
CERTIFICATE OF CORRECTION

PATENT NO. : 5,962,504
DATED: Oct. 5, 1999
INVENTOR(S) : Alan P. Kozikowski It is certified that error appears in the above-identified patent and that said Letters Patent is hereby corrected as shown below:

In column 3, line 31, delete "$R_c$" and insert --$R_e$--, therefore.
In column 3, line 32, delete "$R_c$" and insert --$R_e$--, therefore.
In column 10, line 17, delete "$r^2$" and insert --$R^2$--, therefore.
In column 16, line 19, delete "(td, 1H)," and insert --(td, 1H--, therefore.
In column 16, line 20, delete "br.t, 1H)" and insert --br.t, 1H--, therefore.
In column 16, line 22, delete "br.t, 2H), J=6.9" and insert --br.t, 2H, J=7.2--, therefore.
In column 16, line 23, delete "(d, 3H)," and insert --(d, 3H,--, therefore.
In column 16, line 30, delete "as follows:" and insert --as follows:
a.   N-Boc-4-(4-bromophenyl)-5-(*tert*-butyldimethylsilyoxylmethyl) pyrrolidin-2-one.", therefore.
In column 16, line 56, delete "(br.s," and insert --(d,--, therefore.
In column 16, line 62, delete "-C NMR" and insert --$^{13}$C NMR--, therefore.
In column 17, line 33, delete "-5.39°" and insert ---5.38°--, therefore.
In column 28, line 56, delete "R'" and insert --R"--, therefore.
In column 28, line 60, delete "ins ub-part" and insert --in sub-part--, therefore.
In column 28, line 62, delete "R'" and insert --R"--, therefore.
In column 28, line 67, delete "R'" and insert --R"--, therefore.
In column 29, line 12, delete "6.889d," and insert --6.88 (d,--, therefore.
In column 29, line 39, delete "R'" and insert --R"--, therefore.
In column 30, line 4, after "2.22(m, 1H)", insert --1.86 (dd, 1H,--, therefore.
In column 31, line 30, delete "($C_3$-$C_6$)" and insert --($C_2$-$C_6$)--, therefore.
In column 31, line 34, delete "$C_2$-$C_{15}$ Oalkynl" and insert --($C_2$-$C_{15}$ (alkynyl--, therefore.
In column 31, line 59, after "($C_2$-$C_{15}$)alkynyl" insert --($C_3$-$C_8$)cycloalkyl, ($C_3$-$C_8$)cycloalkyl ($C_1$-$C_{10}$)alkyl--, therefore.

UNITED STATES PATENT AND TRADEMARK OFFICE
CERTIFICATE OF CORRECTION

PATENT NO. : 5,962,504
DATED : Oct. 5, 1999
INVENTOR(S) : Alan P. Kozikowski

It is certified that error appears in the above-identified patent and that said Letters Patent is hereby corrected as shown below:

In column 32, line 12, delete "($C_1$-$C_6$ alkyl" and insert --($C_1$-$C_6$) alkyl--, therefore.
In column 32, line 15, delete "($C_1$-$C_6$ alkyl" and insert --($C_1$-$C_6$) alkyl--, therefore.

Signed and Sealed this

Sixth Day of March, 2001

Attest:

NICHOLAS P. GODICI

Attesting Officer    Acting Director of the United States Patent and Trademark Office